US005463028A

United States Patent [19]
Landry et al.

[11] Patent Number: 5,463,028
[45] Date of Patent: Oct. 31, 1995

[54] REAGENTS FOR GENERATING A POLYCLONAL HYDROLYTIC ANTIBODY RESPONSE AGAINST COCAINE AND THE MONOCLONAL HYDROLYTIC ANTIBODIES AGAINST COCAINE DERIVED THROUGH THESE REAGENTS

[75] Inventors: Donald W. Landry; Kang Zhao, both of New York, N.Y.

[73] Assignee: The Trustees of Columbia University in the City of New York, New York, N.Y.

[21] Appl. No.: 862,801

[22] Filed: Apr. 3, 1992

[51] Int. Cl.$^6$ .............................. C07K 17/02; C07K 16/46
[52] U.S. Cl. .................. 530/405; 530/409; 530/362; 530/363; 530/380; 546/23; 435/188.5
[58] Field of Search ..................... 546/23, 124, 132, 546/22; 530/362, 363, 370, 380, 405, 409, 404, 405; 436/543, 547; 435/188.5

[56] References Cited

U.S. PATENT DOCUMENTS

| | | | |
|---|---|---|---|
| 4,659,567 | 4/1987 | Tramontano et al. | 435/188.5 |
| 4,792,446 | 12/1988 | Kim et al. | 424/85.8 |
| 4,888,281 | 12/1989 | Schochetman et al. | |
| 4,963,355 | 10/1990 | Kim et al. | 424/85.8 |
| 5,030,717 | 7/1991 | Tramontano et al. | 435/188.5 |
| 5,037,750 | 11/1991 | Schochetman et al. | 435/188.5 |
| 5,187,086 | 2/1993 | Janda | 435/188.5 |

OTHER PUBLICATIONS

Kibbe et al (1977) Pharmacological Research Communications 9(4):367–374.
Landry et al (1993) Science 259:1899–1901.
Morell (1993) Science 259:1828.
Aldrich Catalog (1992) p. 468.
Fauci, A. S., (Feb. 1988) The Human Immunodeficiency Virus: Infectivity And Mechanisms of Pathogenesis, *Science*, 239:617–622 (Exhibit I).
Gatley, S. J., et al. (1990), Rapid Stereoselective Hydrolysis of (+)-Cocaine in Baboon Plasma prevents its uptake in the Brain: Implications for Behavioral Studies, *J. Neurochem.* 54:720–723, (Exhibit J).
F. H. Gawin and E. H. Ellinwood, Jr. "Cocaine and other stimulants: Actions, abuse and treatment", New Eng. J. Med. 1988, 318:1173–1182.
L. M. Lesko et al., "Iatrogenous cocaine psychosis", N. Eng. J. Med. 1982, 307:1153.
N. E. Goeders and J. E. Smith, "Cortical dopaminergic involvement in cocaine reinforcement", Science 1983, 221:773–775.
F. H. Gawin et al., "Desipramine facilitation of initial cocaine abstinence", Arch. Gen. Psychiatry 1989, 46:117–121.
F. H. Gawin et al., "Outpatient treatment of 'crack' cocaine smoking with flupenthixol decanoate", Arch. Gen Psychiatry 1989, 46:322–325.
M. W. Fischman, et al., "Effects of desipramine maintenance on cocaine self-administration by humans", J. Pharm and Exper. Therapeu. 1990, 253:760–770.
K. F. Bonese et al., "Changes in heroin self-administration by a rhesus monkey after morphine immunization", Nature 1974, 252:708–710.
A. Tramontano et al., "Catalytic antibodies", Science 1986, 234:1566–1570.
S. J. Pollack et al., "Selective chemical analysis by an antibody", Science 1986, 234:1570–1573.

(List continued on next page.)

*Primary Examiner*—Kay K. A. Kim
*Attorney, Agent, or Firm*—John P. White

[57] ABSTRACT

This invention provides a compound comprising a methyl ecgonine group chemically attached to a phenylphosphonic group which is an analog to an intermediate of the hydrolysis transition-state of a cocaine benzoyl ester group. This invention also provides such analogs linked to carrier proteins, and antibodies thereto.

11 Claims, 1 Drawing Sheet

OTHER PUBLICATIONS

S. J. Benkovic, et al., "Catalysis of a stereospecific bimolecular amide synthesis by an antibody", Proc. Natl. Acad. Sci. USA 1988, 85:5355–5358.

D. Y. Jackson, et al., "An antibody-catalyzed claisen rearrangement", J. Am. Chem. Soc. 1988, 110:4841–4842.

S. J. Benkovic et al., "The enzymic nature of antibody ctaalysis: Development of multistep kinetic processing", Science 1990, 250:1135–1139.

K. D. Janda et al. "Induction of an antibody that catalyzes the hydrolysis of an amide bond", Science 1988, 241:1188–1191.

K. M. Shokat, et al., "A new strategy for the generation of catalytic antibodies", Nature 1989, 338:269–271.

B. L. Iverson and R. A. Lerner, "Sequence-specific peptide cleavage catalyzed by an antibody", Science 1989, 243:1184–1188.

T. Kitazume et al., "Antibody-catalyzed double stereoselection in fluorinated materials", J. Am. Chem. Soc. 1991, 113:8573–8575.

A. G. Cochran, et al., "Antibody-catalyzed biomolecular imine formation", J. Am. Chem. Soc. 1991, 113:6670–6672.

K. D. Janda, et al., "Catalytic antibodies with acyl-transfer capabilities: Mechanistic and kinetic investigations", J. Am. Chem. Soc 1991, 113:291–297.

A. Tramontano, et al., "Chemical reactivity at an antibody biding site elicited by mechanistic design of a synthetic antigen", Proc. Natl. Acad. Sci. 1986, 83:6736–6740.

K. D. Janda et al., "Catalytic antibodies with lipase activity and R or S substrate selectivity", Science 1989, 244:437–440.

A. Tramontano, et al., "Antibody catalysis approaching the activity of enzymes", J. Am. Chem. Soc. 1988, 110:2282–2286.

K. D. Janda et al., "Antibody bait and switch catalysis: A survey of antigens capable of inducing abzymes with acyl-transfer properties", J. Am. Chem. Soc. 1991, 113:5427–5434.

E. Baldwin and P. G. Schultz, "Generation of a catalytic antibody by site-directed mutagenesis", Science 1989. 245:1104–1107.

K. D. Janda et al., "Substrate attenuation: An approach to improve antibody catalysis", Tetrahedron 1991, 47:2503–2506.

I. Fujii, et al., "Enantiofacial protonation by catalytic antibodies", J. Am. Chem. Soc. 1991, 113:8528–8529.

J. Ambre, et al., "Urinary excretion of ecgonine methyl ester, a major metabolite of cocaine in humans", J. Analytical Toxicology 1984, 8:23–25.

J. Ambre, "The urinary excretion of cocaine and metabolites in humans: A kinetic analysis of published data", J. Anal. Toxicol. 1985, 9:241–245.

P. G. Schultz, "The interplay between chemistry and biology in the design of enzymatic catalysts", Science 1988, 240:426–433.

C. B. Carpenter, "Immunosuppression in organ transplantation", N. Engl. J. Med. 1990. 332:1224–1226.

E. J. Ziegler, et al., "Treatment of gram-negative bacteremia and septic shock with HA–1A human monoclonal antibody against endotoxic", N. Engl. J. Med 1991, 324:429–436.

R. D. Mayforth and J. Quintans, "Designer and catalytic antibodies", New Eng. J. Med. 1990, 323:173–178.

L. M. Reichmann et al., "Reshaping human antibodies for therapy", Nature 1988, 332:323–327.

C. Queen et al., "A humanized antibody that binds to the interleukin 2 receptor", Proc. Natl. Acad. Sci USA 1989 86:10029–10033.

M. J. Chow, et al., "Kinetics of cocaine distribution, elimination, and chronotropic effects", Clin. Pharmacol. Ther. 1985, 38:318–324.

S. Ikeda et al., "Asymmetric induction via a catalytic antibody", J. Am. chem. Soc. 1991, 113:7763–7764.

R. A. Dean et al., "Human liver cocaine esterases: ethanol-mediated formation of ethylcocaine", FASEB J. 1991, 5:2735–2739.

M. Benuck et al., "Pharmacokinetics of systemically administered cocaine and locomotor stimulation in mice", J. Pharmacol. Exp. Therap. 1987. 243:144–149.

REAGENTS FOR GENERATING A POLYCLONAL HYDROLYTIC ANTIBODY RESPONSE AGAINST COCAINE AND THE MONOCLONAL HYDROLYTIC ANTIBODIES AGAINST COCAINE DERIVED THROUGH THESE REAGENTS

Within this application, several publications are referenced by arabic numerals within parentheses. Full citations for these publications may be found at the end of the specification immediately preceding the claims. The disclosures of these publications are hereby incorporated by reference into this application in order to more fully describe the state of the art to which this invention pertains.

BACKGROUND OF THE INVENTION

Cocaine has been used by over 30,000,000 Americans since 1980 and frank addiction afflicts at least 1,700,000(1). The medical and social consequences of this stimulant abuse are well known and range from acute psychoses to cardiac failure and from violent behavior to crack-addicted newborns(2–4). Cocaine-induced disinhibition and an increased propensity for high risk behavior now pose a special peril with the advent of the acquired immunodeficiency syndrome (AIDS). The highly reinforcing nature of stimulants makes this form of substance abuse especially pernicious and despite a variety of pharmacologic and non-pharmacologic approaches to treatment, no modality is adequately successful(5,6). The reinforcing potential is clearly related to peak serum concentration(7–9). Also, the rapidity with which the peak is achieved appears critical and may relate to the observation that tolerance to the psychopharmacologic and physiologic effects of cocaine manifests during the course of a single administration(10). rampaging abuse of crack, a smokeable form of cocaine, likely corresponds in part to its rapid delivery across the lung with an efficiency approaching that of an intravenous injection(1,5). Pharmacokinetics may also explain the propensity for binge use associated with crack smoking(1). An agent that reduced the velocity to and magnitude of peak serum levels would permit this hypothesis to be tested as well as have major therapeutic potential.

The neuropharmacologic approach to treatment has focused on receptor systems such as the dopaminergic pathways that mediate the effects of cocaine(11). A direct antagonist to cocaine is not available but agents such as desipramine show some promise for maintaining abstinence(12,13). However, there is a lag of several weeks in the onset of desipramine's effect and during this induction period a marked potential for recidivism remains(5,14). An agent effective even for just this period could have important clinical applications but at present no such agent exists. An alternative to receptor based approaches would be to interfere with the delivery of cocaine to the central nervous system (CNS) so that a dose of cocaine no longer had a reinforcing behavioral effect. Since there is no prospect for excluding cocaine from the circulation, this approach would require binding of cocaine by a circulating agent.

In the 1970's Schuster and colleagues investigated an immunologic approach to substance abuse based on the possibility of interference with CNS delivery(15). A rhesus monkey was allowed to self-administer heroin to dependence, and then was immunized to an opiate. Despite access to the heroin, the animal no longer self-administered it. The serum anti-opiate antibody titer greatly exceeded the cerebrospinal fluid titer and this localized the antibody effect to the serum. Thus, the association of heroin and circulating heroin antibody must have been sufficiently rapid to block the heroin's effect. However, the limitation of the approach was identified in that continued administration of very high doses of heroin exhausted the pool of circulating antibody and the animal resumed heroin self-administration. Thus, the approach worked in that the antibody effectively bound the drug and did modify behavior but the approach was limited in that the antibody supply was exhaustible. An antibody would need the characteristics of an enzyme to avoid being "depleted" itself as it depleted its target.

Recently, the exciting development of catalytic antibodies has been reported(16,17). Catalytic antibodies not only bind but also act as artificial enzymes which metabolize their target thus freeing the antibody for further binding(18–25). The principles of this startling advance are illustrated by considering the hydrolysis of a carboxylic acid ester by an enzyme. As seen in FIG. 1, hydrolysis of the planar ester commonly proceeds through a tetrahedral intermediate which decomposes to yield alcohol and planar carboxylic acid. The rate of the reaction varies with the magnitude of the activation barrier($\Delta G$) between the starting ester and the peak or transition state structure. An enzyme's active site contains a pocket that complements the structure of the hydrolysis transition-state and through various binding interactions, the enzyme stabilizes the transition-state relative to the starting material. This differential stabilization decreases $\Delta G$ and contributes to catalysis. The transition state corresponds to a particular configuration of atoms and is thought to resemble the definable species closest to it in energy, i.e. the tetrahedral intermediate in the case of ester hydrolysis. The transition state is unstable and evanescent but phosphonate monoesters are stable compounds which resemble this species in geometry and distribution of charge and on this basis, may serve as transition state analogs. An antibody elicited to such an analog will manifest binding interactions complementary to the hydrolysis transition state being modeled. This antibody, by binding to the modeled substrate, will stabilize the transition state relative to the starting state, lower the activation barrier and catalyze the hydrolysis. By binding and destroying its target, the catalytic antibody is then freed to bind an additional target. Ample literature precedent supports the use of catalytic antibodies as artificial enzymes for the hydrolysis of esters(16,17, 26–33).

Of all the commonly abused substances, cocaine is the best candidate for this approach. Attached to the ecgonine nucleus of cocaine is a benzoyl ester group which when hydrolyzed results in a virtually inactive product(35,36)—this is one of the pathways of deactivating metabolism in humans(35,36). The transition state of that reaction resembles the tetrahedral intermediate of hydrolysis and can be mimicked by a suitably designed phosphonate ester analog of the hydrolysis transition state of the cocaine benzoyl ester. A subpopulation of the antibodies elicited by this cocaine analog will function as esterases highly specific for cocaine. Thus, the principal impediment to the immunologic approach suggested two decades earlier—the exhaustibility of the circulating antibody—could be overcome. The anti-cocaine catalytic antibody generated

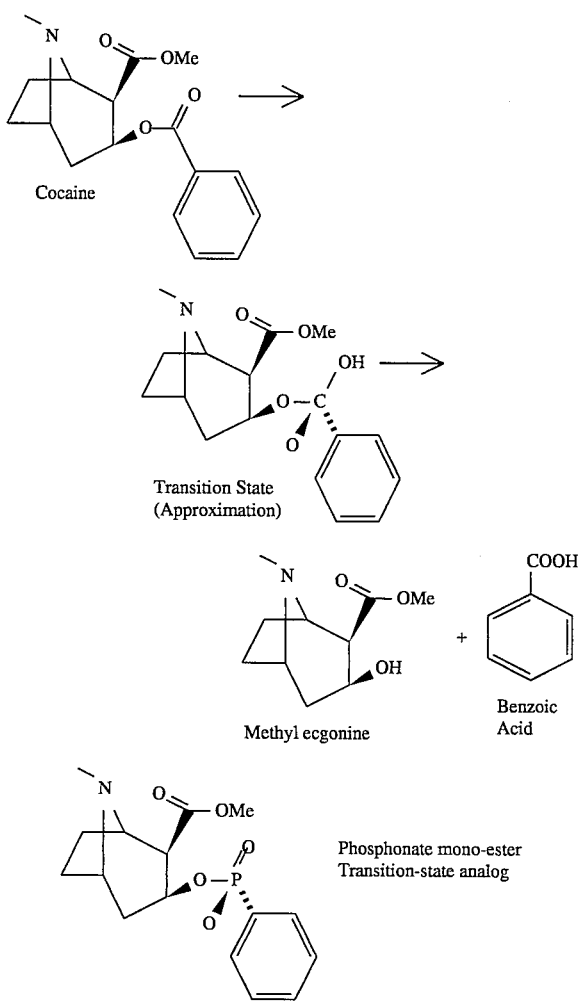

in this fashion would destroy cocaine and be itself available for continued function. The application of such a reagent antibody to the problem of chronic cocaine abuse would be to deprive the abuser of the reinforcing effect of the drug, thereby providing a window for appropriate psychosocial and relapse prevention interventions, and promoting extinction of the addiction.

Only a subpopulation of anti-analog antibodies will possess catalytic activity; so the production of a monoclonal antibody and passive immunization of subjects is required(37,38). Monoclonal antibodies have become established pharmaceutical agents for the treatment of organ transplant rejection(39) and Gram negative septicemia(40). Passive immunization with an anti-cocaine catalytic monoclonal antibody appears to be practical in clinical terms. Second is the duration of effectiveness. The currently available monoclonal pharmaceuticals are administered daily since, as these antibodies bind, the antibody-antigen complexes are removed from the circulation. In contrast, a monoclonal antibody functioning as an artificial enzyme could be designed for longevity(41)—the Fc portion of the antibody genetically engineered for a low clearance rate and portions of the antibody "humanized" by substitution of human in place of mouse epitopes to reduce antigenicity and clearance by a host immune response(42,43). Ideally an administration of an artificial enzyme against cocaine would last for several weeks and provide the extended coverage important for populations with a record of poor compliance.

Third, the efficacy of an artificial enzyme against cocaine relies on a kinetic argument that the rate of cocaine destruction will be able to match the rate of delivery to the CNS. In order to specify the kinetic requirements for the anti-cocaine catalytic antibody, a kinetic model of cocaine delivery is needed. If a dose of smoked crack is absorbed across the lung over the 90–120 second period of one circulation of the intravascular volume (the volume of distribution for the antibody) then an even mixing of cocaine and antibody pools may be assumed. The volume of distribution of cocaine is over twice the total body water(44), but we may neglect this since partitioning of cocaine into other compartments would only decrease on antibody activity. From the moment of cocaine and antibody mixing in the lung, approximately fifteen to twenty seconds elapse before cocaine reaches the CNS capillaries and the most stringent criterion would require complete destruction of cocaine by that time. For a large 100 mg dose (0.36 mmoles) and complete hydrolysis in 15 seconds, the required rate is 0.023 mmol/sec. Thus, the product of the quantity of enzymatic antibody and the antibody's intrinsic enzymatic turnover rate must exceed this value. The assumptions in this model are uniformly conservative and if liberalized would decrease the demand on enzyme performance accordingly. Thus at a monoclonal dose of 200 mg (the monoclonal HA-1A (40) is dosed at 100 mg) the required turnover-rate would be on the order of 2 $sec^{-1}$ to 20 $sec^{-1}$. Catalytic antibodies have been reported with esterase turnover rates from 20–40 $sec^1$ and although these esterases were directed toward particularly susceptible target esters, activity of this order of magnitude is possible(20,29). Also, the $K_m$ values for artificial esterases are as low as 2–15 µM (20,31) less than likely pulmonary venous concentrations of cocaine from crack inhalation. We conclude that the kinetic requirements for a clinically useful anti-cocaine catalytic antibody are attainable. An added advantage is that an antibody suitable for the treatment of addiction by the above criteria could be suitable for the treatment of acute overdose. A final concern is the possibility of saturating the enzyme with massive dosages of cocaine. However, the reinforcing effect of cocaine may not be as significant if peak serum levels are reached more gradually and the large dose of crack may be blunted in effect to a weak dose of nasal cocaine hydrochloride. Thus, the protection afforded by an anti-cocaine enzymatic antibody may not need to be complete in order to be useful.

SUMMARY OF THE INVENTION

The present invention provides a compound having the structure:

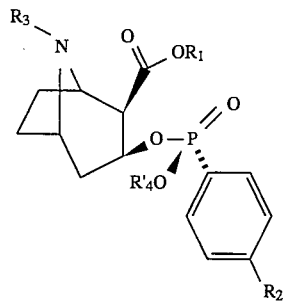

wherein each of $R_1$, $R_2$, $R_3$, or $R_4$ is independently hydrogen, or a lower alkyl; or wherein one but only one of $R_1$, $R_2$, or $R_3$ is a trinitro lower alkyl group, a lower alkyl amine, a group comprising a lower alkyl group linked to a lower alkyl carboxylic acid or derivative, with each of the remaining two of $R_1$, $R_2$, or $R_3$ is independently hydrogen or a lower alkyl and $R_4$ is hydrogen, a lower alkyl or a negative charge.

The present invention provides a compound having the structure:

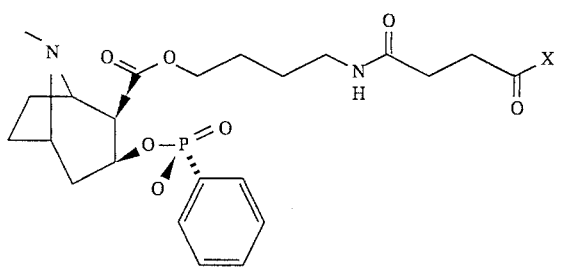

wherein X is a primary amine of a carrier protein.

The present invention provides a compound having the structure:

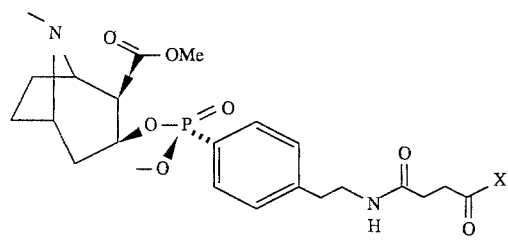

wherein X is a primary amine of a carrier protein.

The present invention provides a compound having the structure:

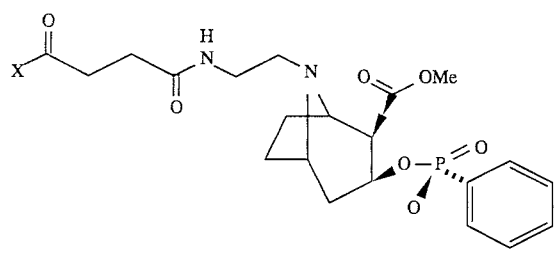

wherein X is a primary amine of a carrier protein.

DETAILED DESCRIPTION OF THE INVENTION

Figure 1:
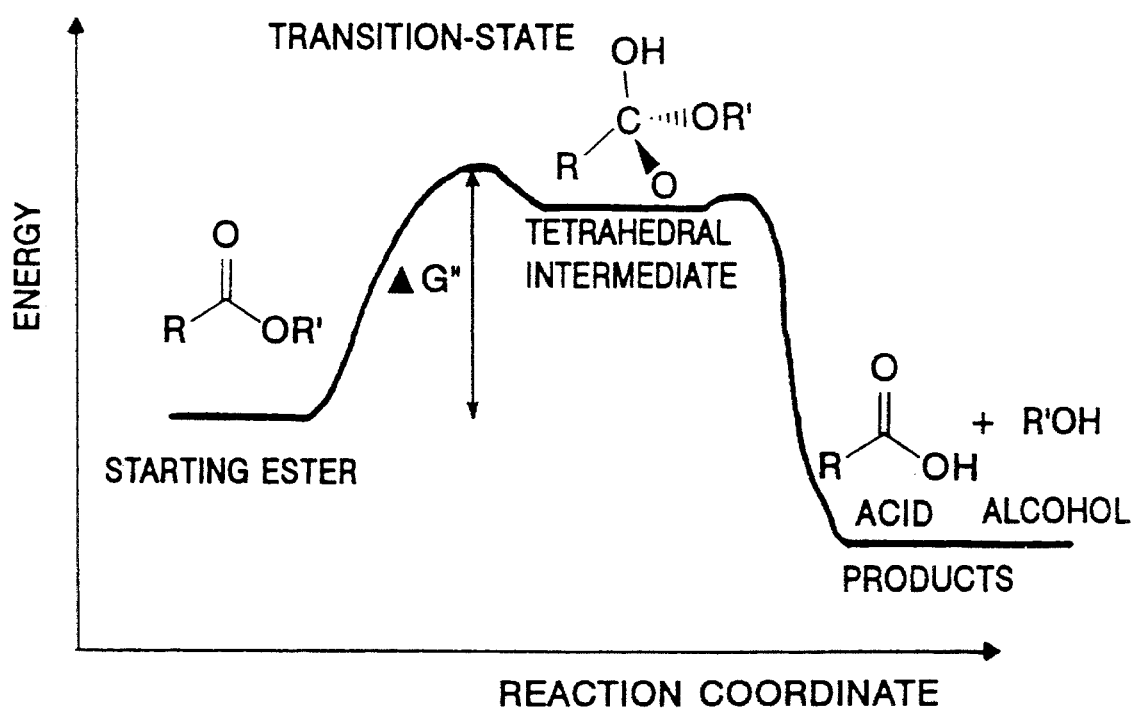
FIG. 1 The kinetic model of the hydrolysis of a carboxylic acid ester. Hydrolysis of the planar ester proceeds through an evanescent tetrahedral intermediate which decomposes to yield alcohol and planar carboxylic acid. The rate of this reaction varies with the magnitude of the difference of the energy states ($\Delta G$) of the starting ester and the peak or transition state structure. The effective catalyst reduces the $\Delta G$ of a reaction and thereby increases the rate of reaction.

The present invention provides a compound having the structure:

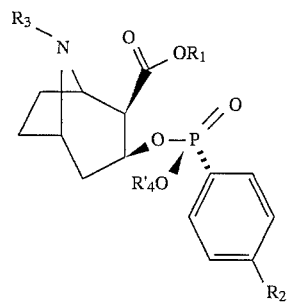

wherein each of $R_1$, $R_2$, $R_3$, or $R_4$ is independently hydrogen, or a lower alkyl; or wherein one but only one of $R_1$, $R_2$, or $R_3$ is a trinitro lower alkyl azide group, a lower alkyl amine, a group comprising a lower alkyl group linked to a lower alkyl carboxylic acid or derivative, with each of the remaining two of $R_1$, $R_2$, or $R_3$ is independently hydrogen or a lower alkyl and $R_4$ is hydrogen, a lower alkyl or a negative charge.

The invention further provides examples of this compound which include but are not limited to the following:

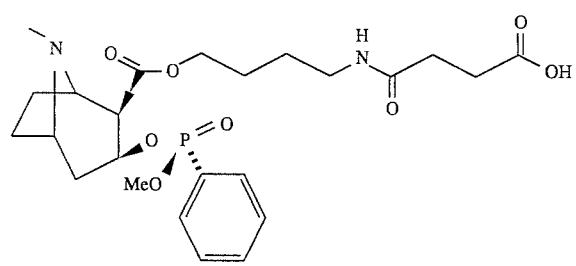

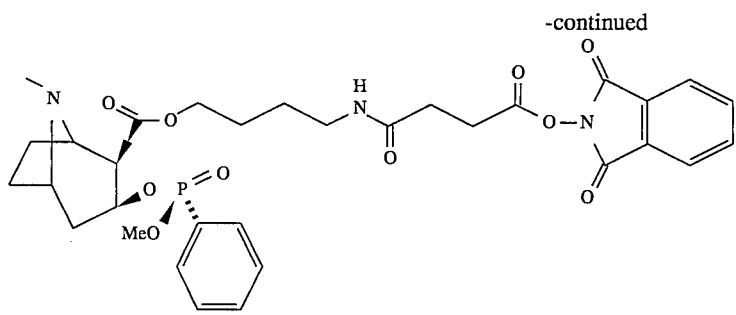

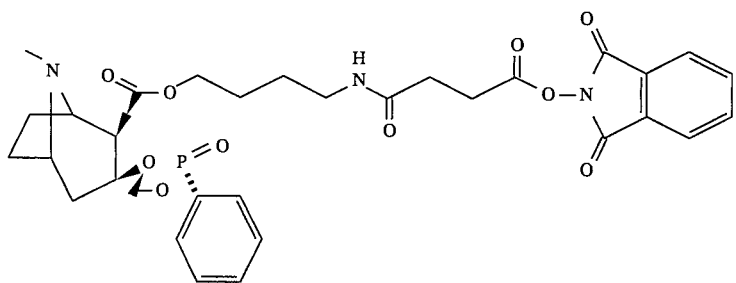

The invention further provides that one but only one of $R_1$, $R_2$, or $R_3$ has the structure:

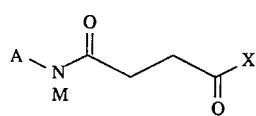

wherein A is a lower alkyl group and X is a primary amine of a carrier protein.

The invention provides for a compound having the structure:

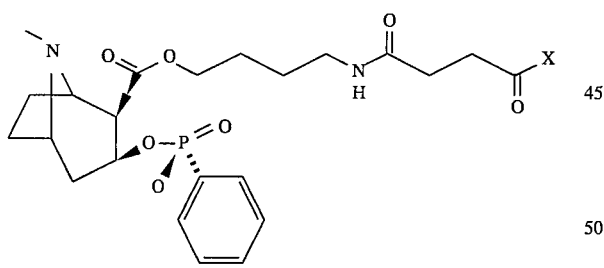

wherein X is a primary amine of a carrier protein. The invention further provides a method of synthesizing this compound comprising selectively alkylating:

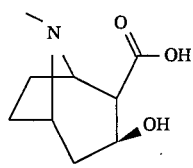

with 4-iodo-n-butyl azide, in the presence of tetraethyl ammonium hydroxide, to yield:

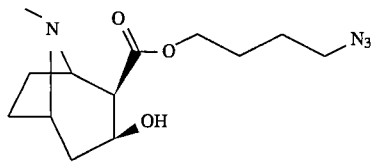

to which was added sequentially an equivalent of phenylphosphonic dicloride and methanol, in the presence of 1H-tetrazole, to obtain:

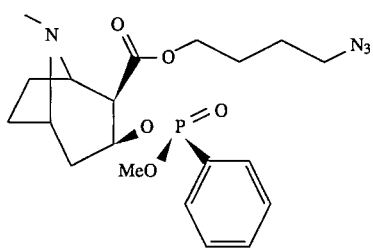

which was subsequently reduced with trimethyl phosphine in benzene to obtain:

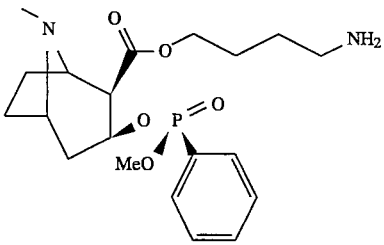

which was acylated with succinic anhydride to obtain:

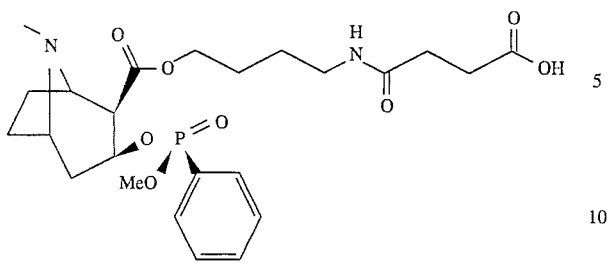

which was converted by acylation with N-hydrophthalimide in combination with dicyclohexylcarbodiimide to:

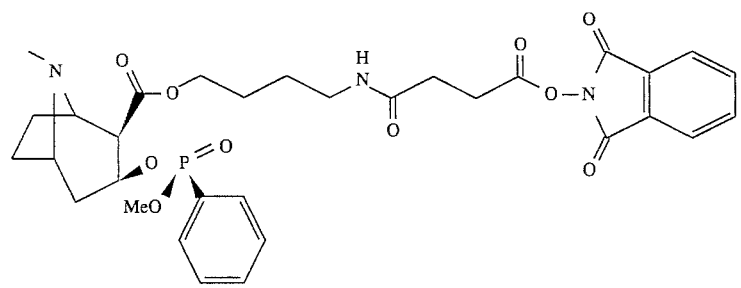

which was selectively dealkylated to:

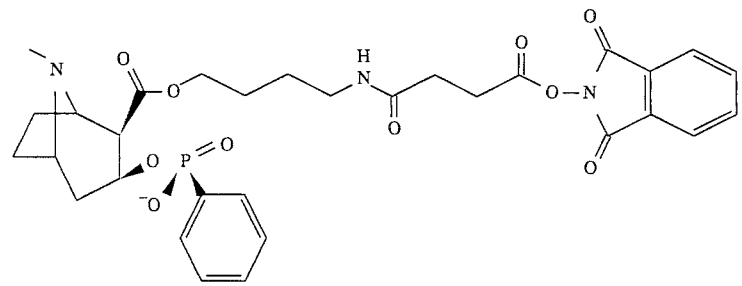

which was coupled to the primary amine of a carrier protein.

The invention provides for a compound having the structure:

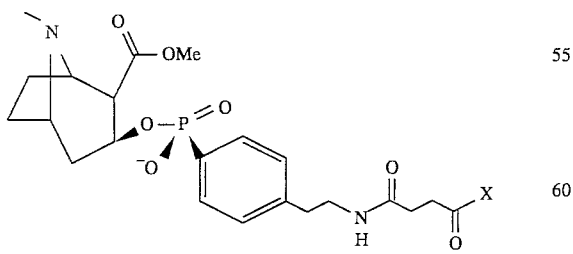

wherein X is a primary amine of a carrier protein. The invention provides a method of synthesizing this compound comprising starting with the structure:

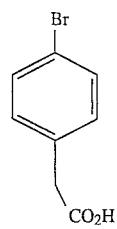

with this acid esterified with acidic methanol and reduced with Dibal(Diisobutylaluminum hydride) to the corresponding alcohol. The alcohol was protected with t-butyldimethylsilyl chloride under imidazole catalysis to yield A:

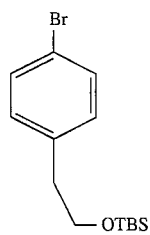

from the starting alcohol. This was transmetalated with n-butyl lithium to the following bromide

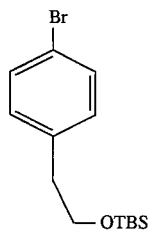

and this structure was phosphorylated with diethylchlorophosphate to yield C:

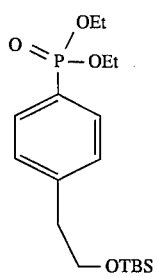

the silyl group of (C) was removed with tetra-n-butylammonium fluoride to yield the corresponding alcohol in 62% yield from (B). This alcohol was transformed to the bromide via tosylate; the phosphonate ester was converted from ethyl to methyl via bromotrimethylsilane followed by methanol; the bromide was displaced by azide; and finally the phosphonate ester was transformed to the phosphorylchloride with the following structure D:

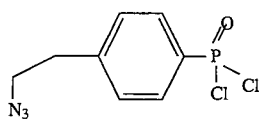

This was in an approximately 30% yield. Using the tetrazole catalysis method, this structure D was coupled with methyl ecgonine:

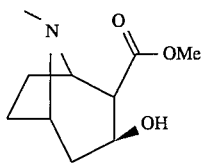

followed by methanol to yield the mixed diester E in 30% yield after column chromatography, having the following structure:

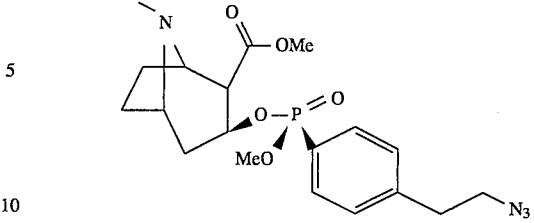

The azide of E was reduced to the corresponding amine with triphenylphosphine and coupled to $^{14}C$ labeled succinic anhydride. The resulting acid was converted to its benzyl ester to facilitate column chromatography in 65% yield from E. The benzyl ester was removed by catalytic hydrogenation, activated by DCC esterification with N-hydroxyphthalimide. Finally, the phosphonate was demethylated with bromotrimethylsilane and the product used directly for coupling to carrier proteins including bovine serum albumin or ovalbumin.

The invention provides for a compound having the structure:

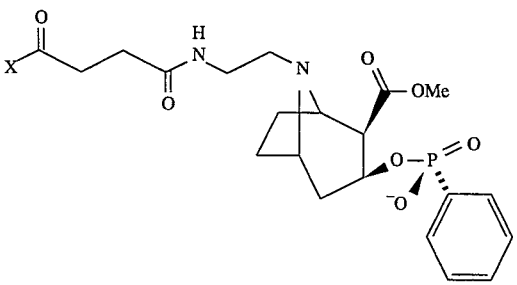

wherein X is a primary amine of a carrier protein.

The invention further provides that the carrier protein is bovine serum albumin, bovine serum ovalbumin, keyhole limpet hemocyanin or thyroglobulin.

The invention further provides antibodies which upon binding to an intermediate of the hydrolysis transition-site of a cocaine benzoyl ester group decreases the ΔG of the hydrolysis reaction. Preferably the antibody is a monoclonal antibody.

The invention further provides a method of decreasing the concentration of cocaine in a subject's blood which comprises administering to the subject an amount of an antibody effective to catalyze hydrolysis of cocaine and thereby reduce the concentration of cocaine in the subject's blood. Preferably the antibody is administered intravenously, yet it is speculated that it can be administered intramuscularly.

This invention is illustrated in the Methods and Materials section which follows. This section is set forth to and in an understanding of the invention but is not intended to, and should not be construed to, limit in any way the invention as set forth in the claims which follow thereafter.

Materials and Methods

1. New Synthetic Method for Phosphonate Monoesters

Hydrolysis of cocaine at either the methyl ester or benzoyl ester yields products that are relatively inactive biologically. Serum and hepatic esterases utilize both metabolic routes and less than 10% of a cocaine dose is excreted unchanged in the urine. The analogs to the hydrolysis of the benzoyl ester are of greater interest since its large hydrophobic phenyl group, as opposed to the small methyl group of the methyl ester, would be more likely to have a significant binding interaction with a complementary binding site of the antibody, and would thus be more likely to elicit an active enzyme. In Scheme II, the hydrolysis of the benzoyl ester of cocaine occurs via a tetrahedral intermediate 1 which can be modeled by the phosphonate monoester 2 and the first objective was the construction

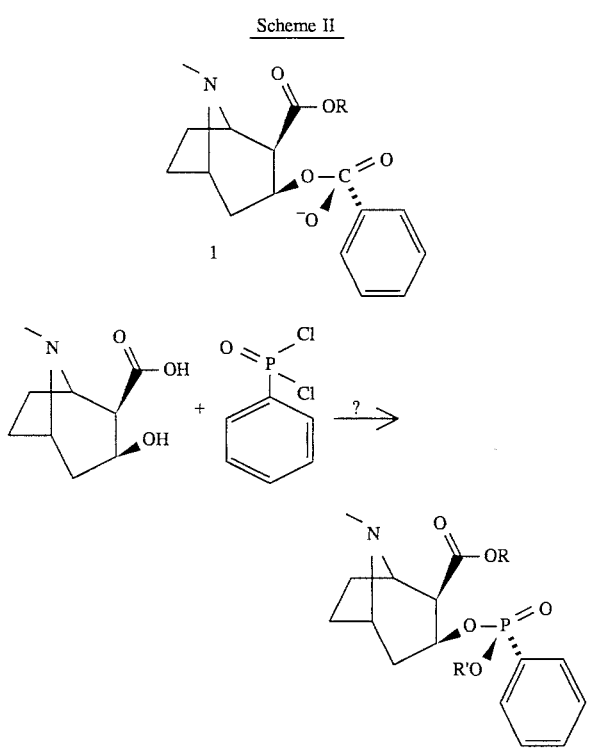

Scheme II of the phosphonate ester linkage. Ecgonine and phenylphosphonic dichloride seemed convenient commercially available starting materials, but none of the literature procedures for the synthesis of phosphonate monoesters was applicable to a hindered, that is, sterically hindered, alcohol such as ecgonine. Phosphonate monoesters are usually protected during synthesis in the form of mixed diesters and revealed by selective dealkylation in the final stages of the work. However, the mixed diesters are best obtained through a multi-step procedure via phosphite intermediates, (45) since their simple preparation through the sequential addition of different alcohols to the phosphonic dichloride provide mixtures of products(46). Hindered alcohols such as menthol (47) react with phosphonic dichlorides very poorly, yielding only about 5% menthyl phosphonic chloride, and under forcing conditions produce corresponding alkyl halide as the major product. Alkoxides of secondary alcohols will react with phosphonic dichlorides(48) or dimethyl phosphonates(49) but yields are variable (15–55%) and the ecgonine nucleus is labile to strong base. All of the above methods were tried with ecgonine and with ecgonine alkyl esters but no more than trace amounts of the desired phosphonate ester were obtained. In order to alter the nature of the reacting species and potentially minimize side reactions, we investigated the coupling of alcohols and phosphonic dichlorides in the presence of catalysts similar to those used for acyl chloride esterification[50]. Neither imidazole nor pyridine had an effect on the ease or course of reaction. However, a catalytic amount of 1H-tetrazole was found to increase the rate of phosphorylation and eliminate conversion of alcohol to alkyl halide.

In a model study, the sequential addition of one

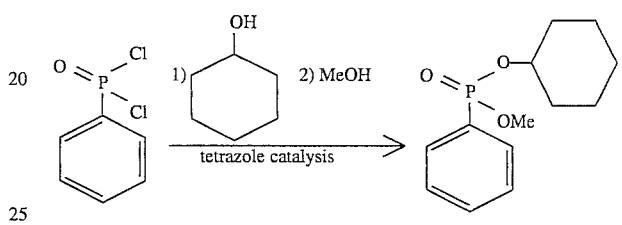

Scheme III equivalent of cyclohexanol and one equivalent of methanol to phenylphosphonic dichloride produced substantial amounts of all three phosphonate diesters (46), confirming that alkyl phosphoryl chlorides are not adequately less reactive than the starting dichlorides. However, in the presence of 1H-tetrazole, the mixed diester was obtained exclusively in 90% yield. Even if both alcohols were primary, the symmetrical diesters were reduced to negligible amounts. Thus 1H-tetrazole enhances the reactivity of the phosphonic dichloride, probably by nucleophilic catalysis, but less effectively catalyzes reaction of the alkyl phosphonyl chloride, perhaps due to increased steric requirements. In conclusion, the tetrazole catalysis method constitutes a simple, high yield route to mixed phosphonate diesters of hindered alcohols. Selective mono-dealkylation would then yield the desired phosphonate mono-ester transition-state analog. All new compounds were satisfactorily analyzed by $^1$H-nmr (200 MHz), infrared and mass spectroscopy with exact mass measurement.

2. Design and synthesis of transition state analogs of cocaine hydrolyses.

The phosphonate ester analog of cocaine hydrolysis specified in Scheme II was only a general structure. Since small molecules do not typically elicit an antibody response, a site for attachment to a carrier protein was required. A point of attachment was chosen based on the ease of synthesis and on sufficient separation from the anticipated locus of hydrolysis. However, the effect of the site of attachment on antigenicity, not to mention catalytic activity, cannot be predicted and the need for several alternatives was anticipated. Our first objective was the compound 3 in Scheme IV since the methyl ester carbonyl of cocaine, although hindered, could be easily modified under relatively mild conditions:

Scheme IV

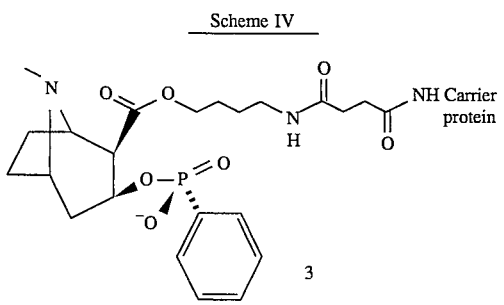

A variety of synthetic schemes were undertaken but analog 3 was ultimately obtained as outlined in Scheme 5. The readily available starting material, ecgonine, was selectively alkylated with 4-iodo-n-butyl azide in the presence of tetraethyl ammonium hydroxide to obtain the ecgonine ester 4 in 92% yield. This hindered secondary alcohol was thus poised for the mixed phosphonic diester synthesis. Commercially available phenyl phosphonic dichloride reacted cleanly under tetrazole catalysis with the alcohol of 4 and after stirring at RT overnight the reaction mixture was quenched with methanol.

Scheme V

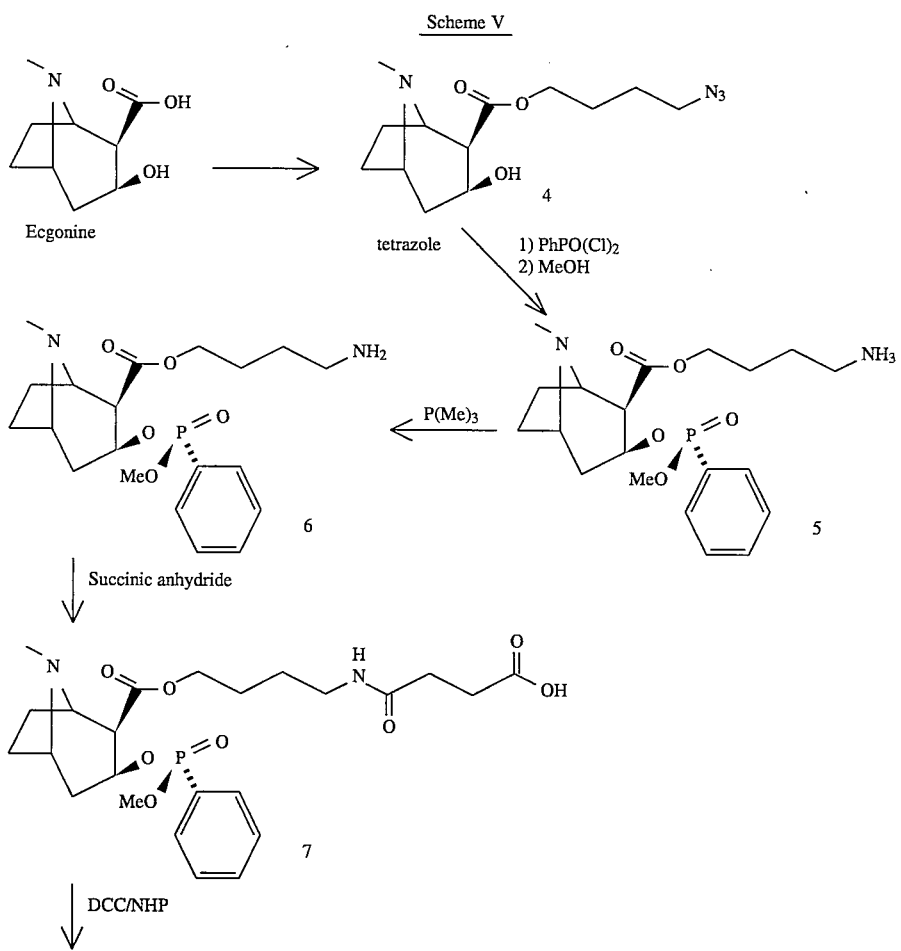

Scheme V -continued

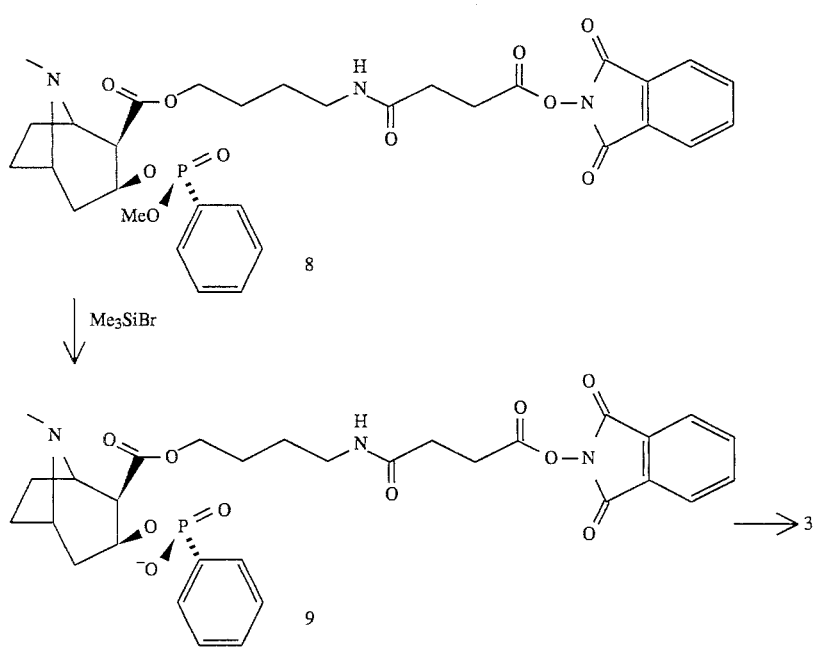

The mixed phosphonate diester 5 was obtained in 80% yield after chromatography on silica gel with methanol as eluent. Thus, the essential core of the transition state analog, protected as the phosphonic diester, was in hand. We completed the side chain for attachment to a carrier protein in three steps. The azide of 5 was reduced with trimethylphosphine in benzene to obtain amine 6 in 82% yield. Amine 6 was then acylated with succinic anhydride. Finally, in anticipation of coupling to a carrier protein, the resulting carboxylic acid 7 was converted to the activated ester 8 by acylation with N-hydroxylphthalimide through the coupling action of dicyclohexylcarbodiimide in 85% yield.

With the phosphonate diester 8 in hand, completion of the synthesis only required selective dealkylation of the methyl phosphonate ester group and coupling of the resulting phosphonate monoester to the 1° amines of a carrier protein. We found the dealkylated product 9 to be unstable but once stabilized by attachment to carrier protein, spectroscopic methods can no longer be used to assess structural integrity. Thus, to demonstrate that dealkylation did not otherwise disrupt the molecule, one aliquot of diester 8 was dealkylated with bromotrimethylsilane and quenched with benzylamine and one aliquot was quenched with benzylamine and then dealkylated. Each path yielded the same product by silica gel thin layer chromatography and $^1$Hnmr spectroscopy suggesting that the dealkylation method was satisfactory. Therefore, the phosphonate 8 was dealkylated with 1.0 equivalent of bromotrimethylsilane in solvent. After 30 min, the reaction mixture containing 9 was evaporated and taken up in a pH8 phosphate buffered solution of bovine serum albumin (1 mg/ml) at 0° C.

The reaction mixture was then subjected to gel filtration chromotography and then dialyzed overnight to yield the desired analog 3. Using $^{14}$C-labeled succinic anhydride, a radiolabeled ester 9 was synthesized and based on the incorporation of $^{14}$C label into 3, the coupling ratio of analog was thus suitable for immunization.

3. DEVELOPMENT OF MONOCLONAL ANTIBODIES AGAINST A TRANSITION STATE ANALOG COCAINE HYDROLYSIS.

Six Balb/C mice were immunized with the analog-carrier 3by both subcutaneous (30 μg) and intraperitoneal (120 μg) routes. Initial immunization was performed with 1:1 Freund's complete adjuvant and boosting injections were administered with incomplete adjuvant at two week intervals. The animals were phlebotomized (200 μL) on day 14 post boost and the plasma was separated from clot and stored at −78° C. For an Eliza assay of the sera, activated cocaine analog used in the immunization was coupled to ovalbumin which has no cross-immunoreactivity with bovine serum albumin. The efficiency of ligand to carrier coupling was 12:1 based on $^{14}$C label incorporation. Plastic 96 well plates were coated with ovalbumin, coupled to analog (4 μg/well) and incubated with dilutions of serum. Goat anti-mouse IgG coupled to horseradish peroxidase was used as the secondary antibody and indicator. Appropriate negative controls included ovalbumin without ligand, non-immune test serum, omission of the test serum and omission of the secondary antibody.

By the third boost, several mice had developed antibody titers of 1:3000. One of these was chosen for hybridoma preparation and boosted by tail vein injection (50 μg, without adjuvant). On day 5 post boost, the animal was sacrificed and the spleen was removed and minced through a mesh screen. The suspension of splenocytes was centrifuged and resuspended, and a portion was assessed using trypan blue dye. Myeloma cells, maintained several days before fusion in complete medium without 8-azaguanine, were washed and combined at a ratio of 1 to 2 with the splenocytes and centrifuged. PEG 1500 was added gently and after an interval, serum free buffer was added in aliquots. The mixture was centrifuged, resuspended and plated on feeder macrophages in complete medium with HAT. Hybridoma colonies were evident by day 5 post fusion. The medium was changed at intervals and on day 15, with colonies confluent, the medium was assayed by Eliza for anti-analog antibodies.

Ten positive colonies were identified and plated to limiting dilution. Seven monoclonals were obtained and samples were obtained and subtyped. None of the anti-analog monoclonals reacted on Elisa with analog-free albumin from mouse or human. Samples were cryopreserved in liquid $N_2$. Repetition of the fusion procedure with a second mouse yielded 23 clones positive for anti-analog antibody.

4. IDENTIFICATION OF MONOCLONAL ANTIBODIES WITH HYDROLYTIC ACTIVITY AGAINST COCAINE

A simple method was devised to screen the monoclonal antibodies for hydrolytic activity against the benzoyl ester linkage of cocaine. Hydrolysis of cocaine at this linkage yields methyl ecgonine and benzoic acid. Acidification of an artificially constituted hydrolysis mixture containing cocaine, methyl ecgonine and benzoic acid with aqueous HCL to pH2, followed by addition of the immiscible organic solvent $CH_2CL_2$ resulted in partitioning of the charged cocaine hydrochloride into the aqueous phase and the neutral benzoic acid into the organic phase. Adding $^{14}C$-benzoic acid to appear in the organic phase with $^{14}C$-benzoic acid. Thus there is no possibility of artifact related to this side reaction.

In order to prepare adequate quantities of the IgG monoclonal antibodies for the enzymatic assay, we prepared malignant ascites. For each line, $2 \times 10^6$ hybridoma cells were placed into a mouse peritoneum which had been pretreated with pristane. After adequate ascites developed, the mice were sacrificed. The ascites was drained and a sample subjected to electrophoresis to assess antibody production. For inadequate responders, the intraperitoneal tumors were minced and injected into a second mouse peritoneum. In the enzyme screen, 250 µL of the each ascites was incubated at 37° C. with 250 µL of 50 mM Na phosphate pH 8.0 containing 1 mM $^{14}C$(aromatic)-cocaine. After 8 hrs. (an extended period since the quantity of antibody was unknown) an aliquot from each was acidified, extracted with $CH^2Cl^2$ and the extract was washed with aqueous acid. Each fraction was subjected to scintillation counting. One of the ascites (1C1-A12) was reproducibly positive and a representative experiment is shown below in Table I.

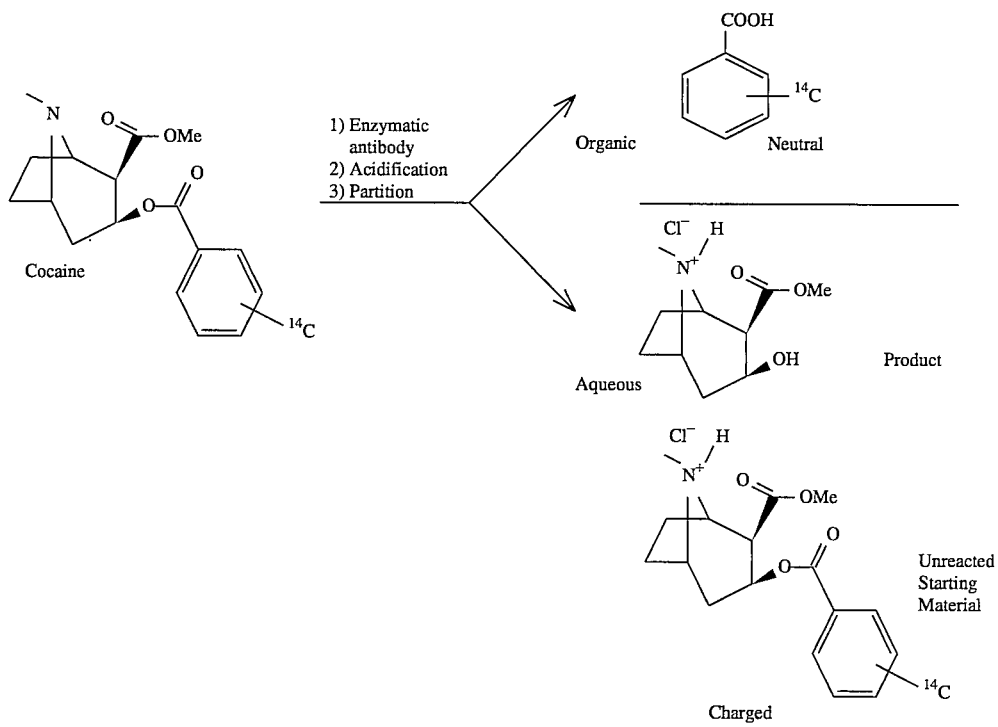

Scheme VI the mixture and using scintillation counting of the partition phases, we estimated the efficiency of the partitioning was estimated to be greater than 97%. $^{14}C$-(aromatic)-cocaine, which we synthesized from methyl ecgonine and $^{14}C$-benzoic acid via dicyclohexylcarbodiimide coupling, partitioned into the aqueous phase with similar efficiency. When $^{14}C$-(aromatic)-cocaine was incubated with a commercial esterase (Sigma) the progress of the reaction could be followed by acidifying aliquots of the reaction mixture, partitioning and counting. In the absence of esterase, the extent of spontaneous hydrolysis in phosphate buffer pH 8.0 at 37° was less than 5% after 12 hrs. Also note that were the methyl ester to spontaneously hydrolyze, then the $^{14}C$-labeled product, benzoyl ecgonine, would be partitioned into the aqueous phase as the hydrochloride salt and would not

TABLE I

|  | Control | 8B8-G4 | 962-H2 | 1C1-A12 |
| --- | --- | --- | --- | --- |
| aq H+ | 2908.0 | 2262.0 | 2226.0 | 286.0 |
| wash | 170.0 | 196.0 | 196.0 | 94.0 |
| organic | 184.0 | 190.0 | 212.0 | 1496.0 |

In contrast to a control without antibody and in contrast to reaction mixtures containing monoclonals 8B8-G4 and 9G2-H2, the reaction containing monoclonal 1C1-A12 resulted in the transfer of counts to the organic phase indicative of cocaine hydrolysis with liberation of benzoic acid. Since the ascites containing 1C1-A12 was non-hemorrhagic and uninfected and since the ascites with 8B8-G4 and 9G2-H2 failed to show esterase activity, mAB 1C1-A12 was likely to be a cocaine benzoyl esterase. Purification of the monoclonal antibody is required to characterize the enzymatic activity and confirm these results.

The experimental data support the methods and the feasibility of the development and evaluation of highly active enzymatic antibodies against cocaine. While the kinetic requirements for an artificial enzyme need not be as stringent for in vivo testing as for clinical use, we nonetheless cannot rely on the first two analogs, not to mention the first catalytic antibody, to be adequate and the literature supports this caution.

5. Organic Chemistry: Design and synthesis of transition-state analogs.

Identifying optimally active catalytic antibodies is a matter of chance and therefore additional analogs may be necessary. Antibodies elicited to the transition-state analog may vary in activity depending on the site of attachment to carrier protein and so the synthesize of additional analogs with an alternative site of attachment to a carrier may be necessary. Variations in the analog structure may elicit antibodies with higher esterase activity against the target and one may synthesize a variety of phenyl-substituted cocaine analogs to investigate the possibility. One may also synthesize novel transition-state analogs that promote intramolecular general acid-base catalysis.

6. Biochemistry: Characterization of artificial enzymes against cocaine.

With two analogs, and others one may synthesize, one may generate monoclonal anti-analog antibodies, study the $K_m$ and the turnover rate of these enzymes to define the practical kinetic limits for this enzymatic reaction and to select candidates for in vivo testing and assess the substrate specificity of these artificial enzymes.

7. Physiology: Investigation of in vivo effects of artificial enzymes against cocaine.

Monoclonal antibodies, selected for activity in vitro, may be prepared and in vivo studies performed in mouse and in rat. One may (i) assess antibody toxicity; (ii) investigate the dose-response relationship for catalytic antibody modification of the direct effects of cocaine administration such as sterotypy.

8. Design and synthesis of transition-state analogs

Literature precedent and the above data support the phosphonate monoester transition-state analog 3 yielding several more catalytic antibodies with hydrolytic activity against cocaine. However, higher activity antibodies may be sought and the rate of success for this search has an element of chance. This stems from the fact that antibodies are elicited to an analog based on the overall antibody-antigen binding affinity whereas catalytic activity requires a much more specific array of binding interactions. A given antibody may bind well and yet lack the full array of interactions needed for strong catalysis. Also, catalytic antibodies that act only by stabilizing the transition state are limited in their rate acceleration ($k_{cat}/k_{uncat}$) to the relative binding affinity of antibody for transition-state (or T.S. analog) vs substrate ($\approx K_m/K_1$)(26). Therefore, in the absence of fortuitous acid-base or covalent catalysis, $k_{cat}/k_{uncat}$ will be low ($10^3$–$10^4$) and $k_{cat}$ and $k_m$ will vary (undesirably) in the same direction. Since our kinetic specifications are demanding, we will attempt to increase the odds of rapidly identifying high activity antibodies by synthesizing and employing additional transition-state analogs. These analogs will be constructed along three lines: (1) use of alternate sites of attachment to carrier proteins; (ii) chemical modifications in the acyl portion of the analog, and (iii) novel transition-state analogs that promote intramolecular acid-base catalysis and could serve as a model for a new generation of transition state analogs.

(i) Alternate site of analog attachment.

The site of attachment on a small molecule to carrier protein affects the antigenicity of the immunogen and specificity in the elicited antibodies. Of particular concern for generating catalytic antibodies, the use of a site on the analog for attachment to carrier protein precludes eliciting antibodies that bind across that site on the actual substrate. For example, the methyl ester of cocaine would be unlikely to occupy a deep binding pocket in an antibody elicited by 3 in Scheme VII.

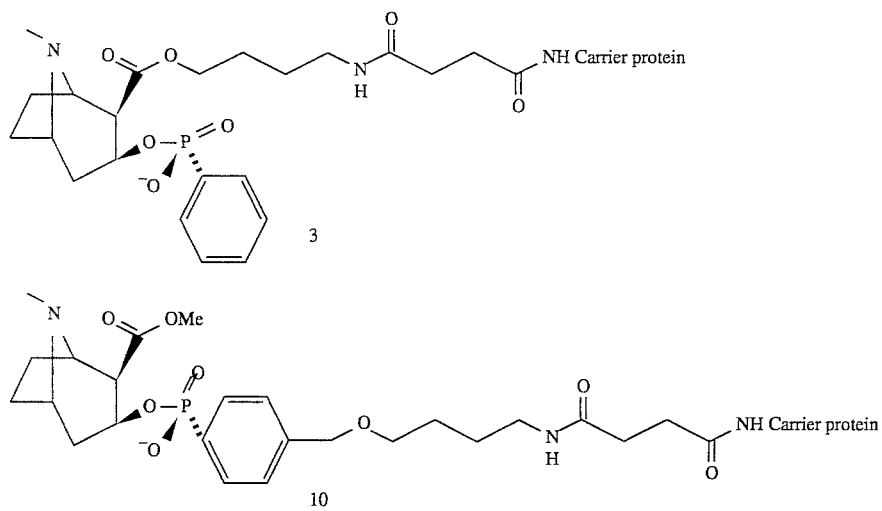

Scheme VII

Scheme VII -continued

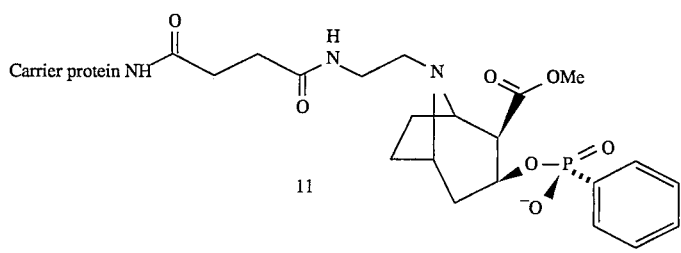

To increase the range of elicited antibodies, we have constructed an analog with alternate sites of attachments including an analog attached at the 4' position of the cocaine aromatic ring 10 and one may construct an analog attached at the cocaine nitrogen analog 11. Each of these new analogs exposes a different surface which has the possibility of eliciting an antibody with the array of binding interactions necessary for hydrolysis. Analog 10 derived from methyl ecgonine and a suitably functionalized phenyl phosphonic dichloride via our tetrazole catalysis procedure. Appropriate reorganization of functional groups yielded the carrier-bound analog as outlined in Scheme VIII.

The transition-state analog 10 was prepared by the route depicted in Scheme VIII. Thus, the commercially available starting material, p-tromophenylacetic acid was esterified with acidic methanol and reduced with Dibal to the corresponding alcohol. The alcohol was protected with t-butyldimethylsilyl chloride under imidazole catalysis to yield A in 86% yield from the starting alcohol. Bromide B was transmetalated with n-butyl lithium and phosphorylated with diethylchlorophosphate to yield C. The silyl group of C was removed with tetra-n-butylammonium fluoride to yield the corresponding alcohol in 62% yield from B. This alcohol was transformed to the bromide via the tosylate; the phosphonate ester was converted from ethyl to methyl via bromotrimethyl silane followed by methanol; the bromide was displaced by azide; and finally the phosphonate ester was transformed to the phosphorylchloride D all in approximately 30% yield. Using the tetrazole catalysis method chloride D was coupled with methyl ecgonine followed by methanol to yield the mixed diester E in 30% yield after column chromotography. The azide of E was reduced to the corresponding amine with triphenylphosphine and coupled to $^{14}C$ labeled succinic anhydride. The resulting acid was converted to its benzyl ester to facilitate column chromatography in 65% yield from E. The benzyl ester was removed by catalytic hydrogenation, and it was activated by DCC esterification with N-hydroxyphthalimide.

Scheme VIII

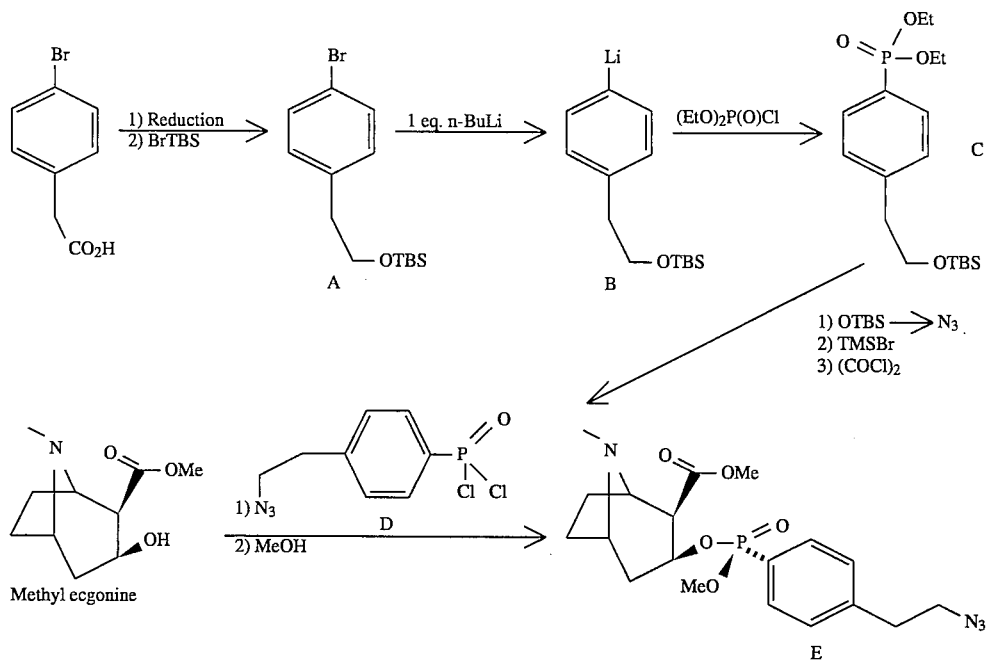

-continued
Scheme VIII

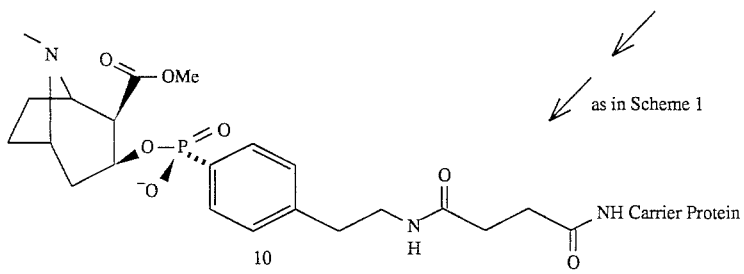

Finally, the phosphonate was demethylated with bromotrimethylsilane and the product used directly for coupling to carrier protein including bovine serum albumin or ovalbumin. Based on the incorporation of radiolabels, the ligand to carrier coupling ratio was approximately 5 to 1.

N-alkylation of a nor-N-methyl ecgonine derivative, either before or after tetrazole catalyzed convertion of the alcohol group to a phosphonate ester, would yield an intermediate easily converted to 11. We would hope to achieve monoalkylation, rather than dialkylation to the quaternary ammonium salt, based on model assessments of steric hinderance but if necessary, we will use a deactivating alkylator such as an α-haloamide. With analogs 3, 10 and 11—all examples of the proven phosphonate monoester strategy for designing transition state analogs—we might expect to eventually obtain the desired high activity enzyme. However, to accelerate this search and to investigate new approaches to transition-state analog design, we will explore additional strategies.

(ii) Acyl modification, substrate attenuation and "bait and switch" strategies. Phosphonate monoester transition-state analogs are typically modeled closely to the structure of the target ester in order to maximize noncovalent binding interactions, and presumably catalytic activity, in the elicited antibodies. However, esterolysis by a catalytic antibody has been demonstrated in one instance to proceed through an acylated antibody intermediate whose hydrolysis was rate-limiting (20). In such a circumstance, structural differences between analog and substrate can increase the overall rate of ester hydrolysis by destabilizing the acyl-antibody intermediate. The general principle of substrate attenuation to increase catalytic efficiency has been recently articulated (32) and the phenyl ring of cocaine is a convenient site for introducing a wide variety of modifications. The phenyl group may be replaced with a heterocycle such as a furanyl group. Alternatively, replacing the phenyl group with a pyridinium group might also elicit a carboxylate group which could provide general base catalysis and this would be a variation on the recently described "bait and switch" strategy for analog design(30). One may synthesize several of these possibilities using the tetrazole catalysis method, mindful of the deleterious effect that excessive substrate attenuation will have on the $K_m$.

Scheme IX

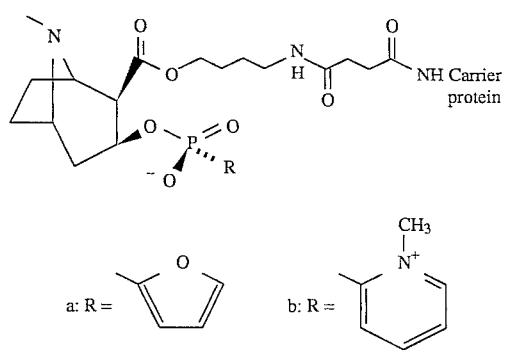

(iii) Induction of intramolecular general acid-base catalysis.

Enzymes achieve high turnover rates through concerted use of several catalytic mechanisms including strain, entropic effects and acid-base catalysis. Catalytic antibodies induced by phosphonate esters may potentially utilize all these mechanisms. However, as alluded to earlier, the antibodies are elicited by overall binding affinity and proper array of interactions for strong catalysis may not be present. However, complex substrates which possess acidic or basic groups suggests a solution to this problem of not being able to specifically control those groups participating in the catalysis. One may properly Scheme X

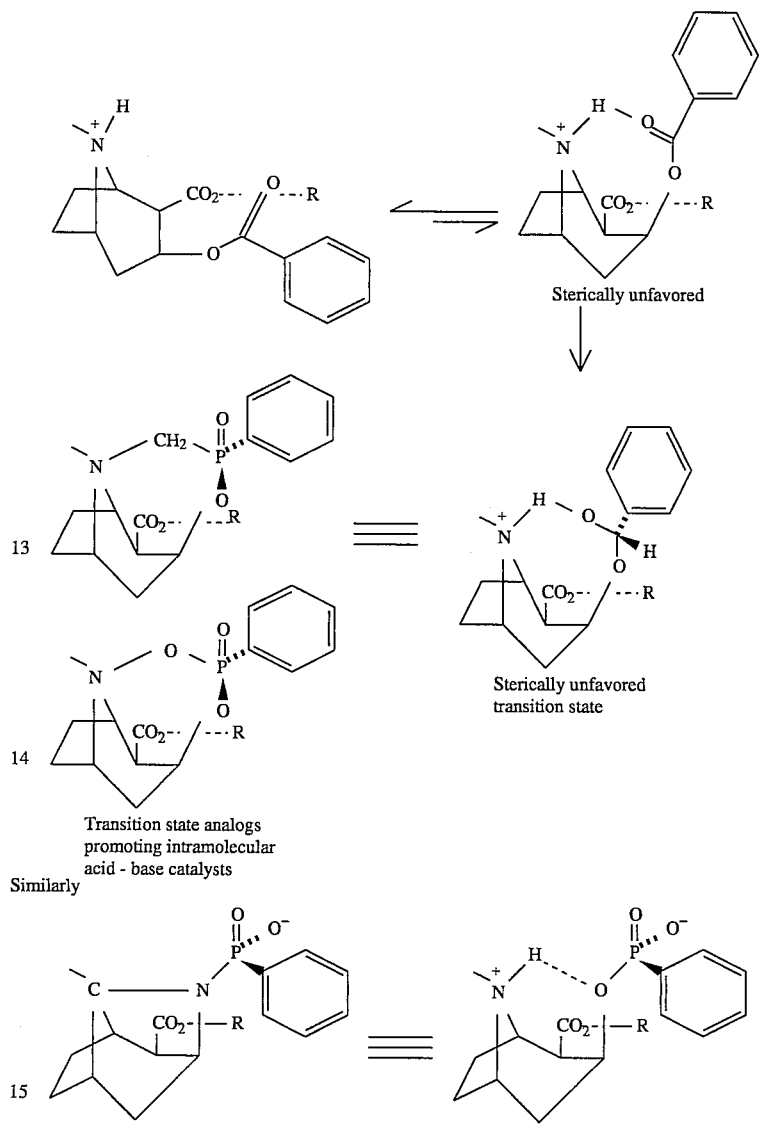

Transition state analogs
promoting intramolecular
acid - base catalysts

Similarly elicit catalytic antibody could, through its overall binding characteristics, position the acidic or basic groups of the substrate itself to provide general acid-base catalysis for the substrate's hydrolysis. For example, the amine of cocaine is protonated to an ammonium ion at physiologic pH and for steric reasons, the proton is oriented toward the benzoyl ester. However, also for steric reasons the benzoyl group is likely to be oriented away from the ammonium group. Nonetheless, an antibody elicited by a transition-state analog such as could, through its overall binding, bring the benzoyl group of cocaine into proximity with the ammonium group and favor intramolecular general acid-base catalysis. For analogs in which carbon is substituted for nitrogen, the corresponding antibody binding pocket would be hydrophobic at this site and this environment would be expected to increase the acidity of the ammonium group and thus increase its capacity to participate in acid catalysis(22). This strategy could increase the efficiency of eliciting catalytic antibodies as well as contribute to a high turnover rate in those identified. Thus, one may construct transition state analogs of general structures 13, 14 and 15 to explore the possibility of rationally directed acid-base catalysis.

Many routes to these analogs are possible. On may anticipate that much exploratory chemistry may be needed. One may anticipate the induction of intramolecular acid-base catalysis to the difficult problem of eliciting artifical enzymes for protein hydrolysis.

9. Characterization of artificial enzymes

One may generate anti-analog antibodies, produce them in quantity through malignant ascites, purify them chromatographically and screen them for enzymatic activity; active enzymes may be examined by kinetic studies to obtain the relevant parameters ($K_m$ and $K_{cat}$) for assessment of in vivo applications; and document enzyme specificity. Subordinate objectives of methodological or theoretical significance include new screening methods for catalytic antibodies and the investigation of catalysis for selected enzymes.

i. Production and identification of enzymatic antibodies

One may generate murine monoclonal antibodies as each transition state analog becomes available according to the methods previously described. Thus, BALB/c mice (6) may be immunized with ligand bound to KLH (100 μg) in adjuvant, boosted at two week intervals and bled 12–14 days after each boost. A mouse with anti-analog titer of at least 1:1000 by Elisa may be sacrificed and the spleen harvested and minced. The splenocytes, after washing and assessment of viability, may be fused with appropriately prepared NSI cells using PEG1500. The cells may be plated over 10 96-well plastic plates and Elisa assay media may identify anti-analog antibody. In order to exclude antibodies with binding activity to the tether used to attach the analog to the carrier for immunization, we may add a control containing just the tether attached to the carrier for the Elisa. The anti-analog antibody producers may be cloned out by the limiting dilution method.

Purification of the anti-analog monoclonals entails production by injecting hybridoma cells into a pristane treated mouse peritoneum followed by precipitation and chromatographic purification. In the standard approach, only then would enzymatic activity be tested for. Initially, one may take this approach for all secretors of anti-analog IgG antibody in order to establish a standard against which to assess early screening approaches. Thus, each malignant ascites may be assessed by gel electrophoresis for a new band indicative of monoclonal antibody production. If response is poor then tumor masses will be lightly minced and reinjected into mice. When response is adequate, the IgG monoclonal antibody may be purified by (a) precipitation with dropwise addition of saturated ammonium sulfate; (b) anion exchange chromotography on DEAE-sephacel with gradient salt elution; and (c) affinity purification on a protein G-sepharose column with conditions as appropriate for the IgG subtype. The purified antibody may be dialyzed into pH 7.4 phosphate reaction buffer and protein concentration determined by a bicinchonic acid (BSA) assay and the molar concentration estimated by assuming a molecular weight of 150,000 for IgG. We may assay aliquots of a reaction mixture constituted with antibody and $^{14}$C-cocaine, at intervals using our assay for benzoyl hydrolysis as described previously. One may also study in detail antibodies resulting in $^{14}$C benzoic acid production over that of a control without antibody.

Development of early screening methods. To identify catalytic antibodies only after ascites formation and antibody purification is time consuming. One approach would be to assay ascites directly for esterase activity in order to avoid chromatography on non-enzymes. Although, as demonstrated hereinabove, ascites per se is not cocaine esterase positive, a concern regarding false positives is justified and not until anti-analog antibodies are purified may one be able to evaluate the false positive and false negative rates. A second approach would be to assess monoclonal supernatants from wingle wells of 96 well plates, thus obviating both ascites formation and chromatography on non-enzymes. As a microscale technique, one may attach $^{14}$C-(aromatic)-cocaine to affi-gel beads using the same site of attachment and same tether as for the analog (3) that elicited the antibody. Incubation of the beads bearing labeled cocaine and the hybridoma medium overnight followed by mechanical separation of the medium for scintillation counting of released $^{14}$C benzoic acid would provide a measure of anti-cocaine hydrolytic activity. In either early screening approach, if false positives were detected, we would repeat the assay with fluoride and eserine, inhibitors of natural esterases.

ii. Kinetic Studies.

One may study the steady-state kinetics of active enzymes by standard methods to obtain the parameters $K_m$ and $k_{cat}$ (turnover rate) relevant to clinical use as described previously. One may observe saturation kinetics and inhibition by analog with all antibodies. Thus, purified monoclonal antibody as obtained above will be diluted into ½ ml of 500mM EPPS pH 7.4, 100 mm NaCl to a final protein concentration of 0.1 μM–10 μM. No co-solvents are anticipated and the temperature will be maintained at 37°±0.1° C. $^{14}$C-(aromatic) cocaine from a stock ethanol solution will be aliquoted, evaported, taken up in ½ cc of identical EPPS buffer and at time zero added to the enzyme at a final cocaine concentration of 0.5 mM–5 mM. Aliquots may be removed at intervals and quenched by dilution into pH2 HCl with partitioning of $^{14}$C-benzoic acid and scintillation counting as described previously. Initial linear rates may be measured (<5% hydrolysis of total substrate). The observed rate may be corrected for the minor spontaneous hydrolysis rate. Kinetic parameters $V_{max}$ and $K_m$ may be determined by non linear least-square fitting of the initial rate vs substrate concentration to a curve described by the Michaelis-Menten equation.

Elucidation of Mechanisms of Catalysis.

For the most active enzyme, particularly if elicited by one of the novel analogs, the detailed mechanism of catalysis would be of theoretical interest. One may localize the catalytic activity to the $F_{ab}$ fragment. One may gain insight into the participating functional groups of the enzyme by analysis of the pH dependence of $k_{cats}$ and by the effect of amino acid-specific chemical modification. Labeling studies such as with $^{18}OH_2$, will confirm a tetrahedral intermediate and $D_2O$/pH dependence analysis may suggest a multistep process. A detailed mechanistic analysis and rationally designed site-directed mutagenesis may be needed to generate a pharmaceutical grade artificial enzyme.

iii. Specificity of the catalytic antibodies.

The substrate specificity of catalytic antibodies is generally excellent and reflects the power of immunorecognition. However, the effect of natural cocaine metabolites such as methyl ecgonine and nor-N-methyl ecgonine, whether as substrates or inhibitors must be assessed. Also, ethyl cocaine has recently been identified as an active cocaine metabolite in those who co-abuse ethanol and cocaine (51). An analog such as 3 would be very likely to elicit catalytic antibodies that would accept ethyl cocaine as a substrate. However, the antibodies derived from analogs with the methyl ester of cocaine intact are less predictable and we will synthesize $^{14}$C-ethyl cocaine and study its hydrolysis by the artificial enzymes directly.

Synthesis of analogs and kinetic analyses would continue until one identified an artificial enzyme with in vivo effectiveness as discussed below.

3. Investigation of in vivo effects of artificial enzymes against cocaine.

A catalytic antibody against cocaine with a turnover rate of less than 0.2 sec$^{-1}$ and a Km of greater than 50 μM might still be clinically useful as outlined and would certainly be a candidate for an in vivo study. In fact, at least initially one may test in vivo all active enzymes. Since the capacity to metabolize cocaine is a function of both the intrinsic activity of the antibody and the quantity of antibody present, increased antibody doses can compensate within practical limits for lower activity. The practical limits include the volume of infusate, the solubility of the protein and the viscosity of the solution. In order to avoid the complication of antibody clearance via a host response, in vivo studies may be restricted to Balb/C mice with the one exception being an assay requiring frequent blood drawing. Since the artificial enzyme approach relies on interception of cocaine before it partitions into the CNS, a blunting of the magnitude and rate of rise of serum cocaine levels appear to be the best measure of efficacy. This approach finesses the vexed question of the suitability and interpretability of the various animal models of cocaine reinforcement. One may examine the capacity of the artificial antibodies to alter direct effects of cocaine administration. One may subject candidate artificial enzymes to the (i) assessment of the direct toxicity of the antibody to mice (ii) modulation of blood cocaine levels in vivo both for acute and, if successful, late-term and chronic cocaine administration (iii) alteration of sterotyping threshold and pattern.

i. Antibody toxicity in mouse

In this set of experiments, male and female BALB/c mice of 15–20 g. One may run toxicity tests in randomly selected groups of 4 males and 4 females infused i.v. with a fixed dose of antibody preparation. One may start with a dose of 20 mg/kg and if toxicity is observed, then one may decrease the dose to determine the threshold. A total of 3 groups of 4 males and 4 females may be tested at a given dose of antibody. Control animals may receive i.v. saline. One may examine all animals for changes in their gross appearance and behavior. Double-blind observations may be rated from 1–5 by two observers.

Qualitative observations of behavior.

One may conduct observations twice daily, at 10:00 AM and at 3:00 PM, for 15 min. each time. Among the subjectively observed parameters include: the condition of the fur, skin vibrissae, eyes and tail, frequency and character of excreta, response to handling, activity in home cage, body tonus and tremors, if any, social interactions, spontaneous motility, grooming behavior, rotary motions and other indicia of sterotypy. The qualitative observations will be confirmed by quantitative measurements of weight, fluid intake, locomotor activity, seizure activity, if any, and neuronal deficits, if any.

Specific quantitative toxicology tests.

General. One may record weight change and fluid intake daily at 10:30 AM.

Locomotor activity: One may test animals in a 4-channel automated Opto-Varimex Mini (Columbus Instruments, Columbus, Ohio)

Total daily activity: One may keep individual animals for 24 hrs in activity cages equipped with a rotating drum and a revolution counter.

Neurological deficit/motor impairment (estimation of a toxic dose): A dose of the antibody which causes half the animals to fall off the rotorod apparatus (Ugo Basile, Comerio, Italy) would be rated as 50% toxic or TD-50. Such toxicity is not anticipated.

ii. The effect of catalytic antibodies on serum cocaine levels.

One may investigate the effect of anti-cocaine catalytic antibody on serum cocaine levels in two assays. A protocol in rat may allow assay at multiple early time points but may be restricted to acute antibody administration due to the possibility of a host versus antibody reaction. An assay in mouse may yield a less detailed serum cocaine profile but may be adaptable to long-term studies. The serum samples may be assayed for cocaine by standard methods (44) acid-base extraction and quantitative gas chromatography with comparison against standards.

Cannulated Rat Model.

The clinical efficacy of the artificial enzyme may depend on altering cocaine peak height or simply the rate of rise to the peak. Thus one may require a protocol providing good time resolution. The mouse is not suitable for multiple blood withdrawals but a rate with a central venous/right heart catheter would suffice and this method is standard (55). Thus adult CD COBS rat, 200–225 g, may be anesthetized with diethyl ether. The superior cranial surface and a metal plate with attachment for a sheath and a central catheter cemented to the bone with epoxy resin. The skin of the superior ventral thorax may be incised and dissected to expose the right external jugular vein. Loose ligatures may be placed around the vein. The flexible plastic catheter may be threaded through the opening of the metal plate and tunnelled under the skin to the superior thorax. The internal jugular may be incised between the ligatures after tying off the superior one. The catheter may be threaded into the jugular to the right atrium and the lower ligature may be tied to secure it. One may flush the catheter with heparin and the incision closed. After the animal has recovered from surgery, it would receive an i.v. injection of the antibody and one hour later an i.v. injection (tail) of cocaine. Blood samples of 40 $\mu$l–100 $\mu$l may be withdrawn every 15–30 sec, treated with dilute acid to stop further enzymatic activity and preserved on ice for analysis. One may compare the serum cocaine profile of control animals with that of animals pretreated with the antibody for differences in peak level, rate of rise to the peak and duration of 50+% peak level. The dose of antibody and the dose of cocaine will be varied independently to define the dose-response relationships.

Mouse Model.

A cannulated rat assay may demonstrate a difference between antibody-treated and untreated animals in terms of the cocaine peak height, time to peak, or duration of >50% peak level, if so, then one may pursue similar measurements in mouse where the time-resolution will be poorer. One may separate BALB/c mice, male and female, 15–25 g, at random into groups of 4 males and 4 females. Half the animals may receive an i.v. injection of the antibody, half may receive saline, all may receive a single subcutaneous injection of cocaine 1 hr. after the antibody. Groups would be guillotined at 3,6,9,12 and 15 min. after cocaine administration and exsanguinated from the heart for cocaine assay. The interval between administration of the antibody and the cocaine would be increased to define the duration of enzyme effectiveness.

iii. Effect of the antibody on cocaine toxicity in vivo.

If one observes an alteration in the serum cocaine profile and if the antibody itself is not toxic at the effective dose, then an almost unlimited range of behavioral experiments may be possible. One may begin with the simplest—the blocking of an acute, direct effect of cocaine. Thus BALB/c mice selected and treated with the antibody (at a dose demonstrated to modulate the serum cocaine profile) or saline as above may receive one hour later a notice of intravenous cocaine previously demonstrated to elicit sterotypy in 50% of untreated animals(56). A shift in the threshold for the cocaine-induced behavior would be sought.

Statistical Analysis.

All values will be presented as means±SD. One way ANOVA will be performed on all sets of data. Where the F-values indicate significant differences ($p<0.001$), all combinations of paired Student t values will be calculated to obtain significant differences between treated and control groups.

References

1. Gawin, F. H., E. H. Ellinwood, Jr. "Cocaine and other stimulants: Actions, abuse and treatment", *New Eng. J. Med.* 318: 1173–1182 (1988).
2. L. L. Cregler and H. Mark. "Medical complications of cocaine abuse", *N. Engl. J. Med.* 315:1495–1500 (1986).

3. J. M. Isner et al., "Acute cardiac events temporally related to cocaine abuse", *N. Engl. J. Med.* 315:1438–1443.
4. L. M. Lesko et al., "Iatrogenous cocaine psychosis", *N. Eng. J. Med.* 307:1153, (1982).
5. C. E. Johanson and M. W. Fischman, "The Pharmacology of cocaine related to its abuse", *Pharm. Rev.* 41:3–52 (1989).
6. H. Kleber and F. Gawin, "Psychopharmacological trials in cocaine abuse treatment", *Am. J. Drug Alcohol Abuse* 12:235–246 (1986).
7. J. I. Javad et al., "Cocaine plasma concentration: Relation to physiological and subjective effects in humans", *Science* 209:227–228 (1978 ).
8. M. D. Wilson, et al., "Psychomotor stimulant self-administration as a function of dosage per injection in the rhesus monkey", *Psychopharmacologic* 29:271–281 (1971).
9. M. W. Fischman and C. R. Schuster. "Cocaine self-administration in humans", *Federation Proc.* 41:241–246 (1982).
10. M. W. Fischman, et al., "Acute tolerance development to the cardiovascular and subjective effects of cocaine", *J Pharm and Experi. Therapeu.* 235:677–682 (1985).
11. N. E. Goeders and J. E. Smith, "Cortical dopaminergic involvement in cocaine reinforcement", *Science* 221:773–775 (1983).
12. F. H. Gawin et al., "Desipramine facilitation of initial cocaine abstinence", *Arch Gen Psychiatry* 46:117–121 (1989).
13. F. H. Gawin et al., "Outpatient treatment of 'crack' cocaine smoking with flupenthixol decanoate." *Arch Gen. Psychiatry* 46:322–325 (1989).
14. M. W. Fischman, et al., "Effects of desipramine maintenance on cocaine self-administration by humans", *J. Pharm. and Exper. Therapeu.* 253:760–770 (1990).
15. K. F. Bonese et al., "Changes in heroin self-administration by a rhesus monkey after morphine immunization", *Nature* 252:708- (1974)
16. A. Tramontano et al., "Catalytic antibodies", Science 234:1566–1570 (1986).
17. S. J. Pollack, et al., "Selective chemical catalysis by an antibody", *Science* 234:1570–1574 (1986).
18. S. J. Benkovic, et al., "Catalysis of a sterospecific bimolecular amide synthesis by an antibody", *Proc Natl Acad. Sci* 85:5355–5358 (1988).
19. D. Y. Jackson, et al., "An antibody-catalyzed claisen rearrangement", *J. Am. Chem. Soc.* 110:4841–4842 (1988).
20. S. J. Benkovic et al., "The enzymic nature of antibody catalysis: Development of multistep kinetic processing", *Science* 250:1135 (1990).
21. K. d. Janda et al. "Induction of an antibody that catalyzes the hydrolysis of an amide bond", *Science* 241:1188–1191 (1988)
22. K. M. Shokat, et al., "A new stratgey for the generation of catalytic antibodies", *Nature* 338:269–271 (1989).
23. B. L. Iverson and R. A. Lerner, "Sequence-specific peptide cleavage catalyzed by an antibody", *Science* 243:1184–1188 (1989)
24. T. Kitazume, et al., "Antibody-catalyzed double steroselection in fluorinated materials", *J. Am. Chem. Soc.* 113:8573–8575 (1991).
25. A. G. Cochran, et al., "Antibody-Catalyzed biomolecular formation", *J. Am. Chem. Soc.* 113:6670—6672 (1991).
26. K. D. Janda, et al., "Catalytic antibodies with acyl-transfor capabilities: Mechanistic and kinetic investigations", *J. Am. Chem. Soc.* 113:291–197 (1991).
27. A. Tramontano, et al., "Chemical reactivity at an antibody binding site elicited by mechanistic design of a synthetic antigen", *Proc. Natl. Acad. Sci.* 83:6736–6740 (1986).
28. K. D. Janda et al. "Catalytic antibodies with lipase activity and R or S substrate selectivity", *Science* 244:437–440 (1989)
29. A. Tramontano et al., "Antibody catalysis approaching the activity of enzymes", *J Am Chem. Soc.* 110:2282–2286 (1988).
30. K. D. Janda et al., "Antibody bait and switch catalysis: A survey of anigens capable of inducing abzymes with acyl-transfer properties", *J. Am. Chem. Soc.* 113:5427–5434 (1991).
31. E. Baldwin and P. G. Schultz, "Generation of a catalytic antibody by site-directed mutagenesis", *Science* 245:1104–1107 (1989).
32. K. D. Janda, et al., "Substrate attenuation: An approach to improve antibody catalysis", *Tetrahedron* 47:2503–2506 (1991).
33. R. A. Fujii, et al., "Enantiofacial protonation by catalytic antibodies", *J. Am. Chem. Soc.* 113:8538–8529 (1991).
34. R. D. Spealman, et al., "Effects of cocaine and related drugs in nonhuman primates II stimulant effects on schedule—control behavior", *J. Pharmacol. Exp. Ther.* 251:142–149.
35. J. Ambre, et al., "Urinary excretion of ecgonine methyl ester, a major metabolite of cocaine in humans", *J. Analytical Toxicology* 8:23–25 (1984).
36. J. Ambre, "The urinary excretion of cocaine and metabolites in humans: A kintic analysis of published data", *J. Anal Toxicol* 9 241–245 (1985).
37. R. A. Lerner, et al., "At the crossroads of chemistry and immunology: Catalytic antibodies", *Science* 252:457–458 (1987)
38. P. G. Schultz, "The interplay between chemistry and biology in the design of enzymatic catalysts", *Science* 40:426–433 (1988).
39. C. B. Carpenter, "Immunosuppress ion in organ transplantation", *N. Engl. J. Med.* 332:1224–1226 (1990).
40. E. J. Ziegler, et al., "Treatment of gram-negative bacteremia and septic shock with HalA human monoclonal antibody against endotoxin", *New Eng. J. Med.* 324:429–436 (1991).
41. R. D. Mayforth and J. Wuintans, "Designer and catalytic antibodies", *New Eng. J. Med.* 323:173–178 (1990).
42. L. M. Reichmann et al., "Reshaping human antibodies for therapy", *Nature* 332: 323–327 (1988).
43. C. Queen et al., "A humanized antibody that binds to the interleukin 2 receptor", *Proc. Natl. Acad. Sci. USA* 86:10029–10033 (1989).
44. M. J. Chow, et al., "Kinetics of cocaine distribution elimination, and chronotropic effects", *Clin. Pharacol. Ther.* 38:318–324 (1985).
45. T. L. Emmick and R. L. Letsinger, "Unsymmetrical secondary phosphine oxides. Synthetic, isotopic exchange, and sterocehmical studies", *J. Am. Chem. Soc.* 90:3459 (1968).
46. Y. Nitta and Y. Arakawa, "The selective dealkylation of maed esters of phosphoric acid and phenyl phosphonic acid using cation exchange resin", *Chem. Pharm. Bull.* 34:3121 (1986).
47. R. J. P. Corriu et al., "Recent developments in Methods for the esterification and protection of the carboxyl group", *Tetrahedron* 36:1617 (198).
48. H. Duddeck and R. Lecht, "Synthesis and NMR spectroscopic investigation of phenyl phosphoryl derivatives", "Phos. and Sulfur", 29:169 (1987).
49. S. Keda et al., "A Symmetric induction via a catalytic antibody", *J. Am. Chem. Soc.* 113:7763 (1991).

50. W. P. Reeves and M. L. Bahr, "Phase-transfer catalysis; Preparation of alkyl azides", *Synth* 823 (1976).
51. R. A. Dean, et al., "Human liver cocaine esterases:ethanol-mediated formation of ethylcocaine", *FASEB J.* 5:2735–2739 (1991).
52. D. W. Landry. "Total synthesis of 8S, 14-cedranediol", *Tetrahedron* 39:2761 (1982)
53. D. W. Landry, et al., "Epithelial chloride channel Development of inhibitory ligands", *J. Gen. Physiol.* 90:779–798 (1987).
54. D. W. Landry, et al., "Purification and reconstitution of chloride channels from kidney and trachea", *Science* 244:1469–1472 (1989).
55. G. S. Tannenbaum and J. B. Martin, "Evidence for an endogenous ultradian rhythm governing growth hormone secretion in the rat", *Endocrinology* 98:562–570 (1976).
56. M. Benuck, et al., "Pharacakinetics of systemically administered cocaine and locomotor stimultion in mice", *J Pharmacol Exp Therap.* 243:144–149 (1987).

What is claimed is:

1. A compound having the structure:

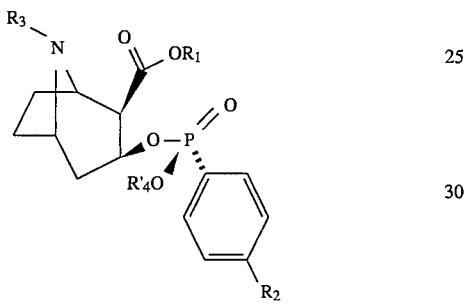

wherein each of $R_1$, $R_2$, $R_3$ or $R_4$ is independently hydrogen, or a lower alkyl; or wherein one but only one of $R_1$, $R_2$ or $R_3$ is an alkyl azide group, a lower alkyl amine, a group comprising a lower alkyl group linked to a lower alkyl caboxylic acid or derivative, with each of the remaining two of $R_1$, $R_2$ or $R_3$ is independently hydrogen or a lower alkyl and $R_4$ is hydrogen, a lower alkyl or a negative charge.

2. The compound of claim 1 having the structure:

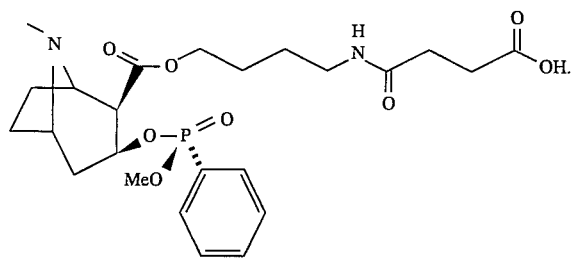

3. The compound of claim 1 having the structure:

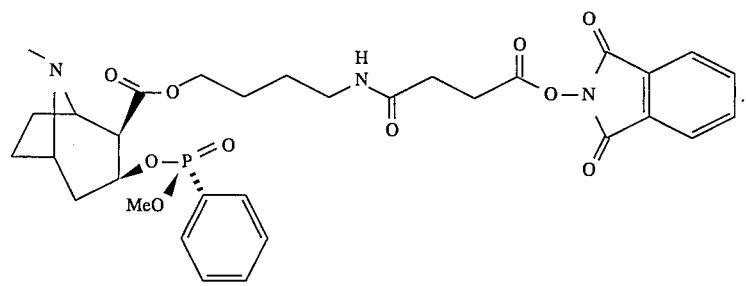

4. The compound of claim 1 having the structure:

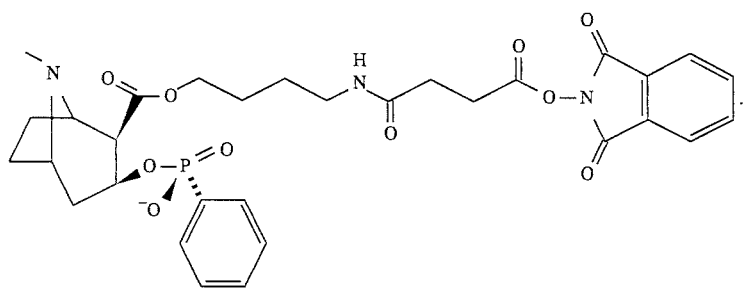

5. The compound of claim 1 attached to a protein, wherein one but only one of $R_1$, $R_2$, or $R_3$ has the structure:

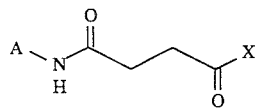

wherein A is a lower alkyl group and X is a primary amine of a carrier protein.

6. A compound having the structure:

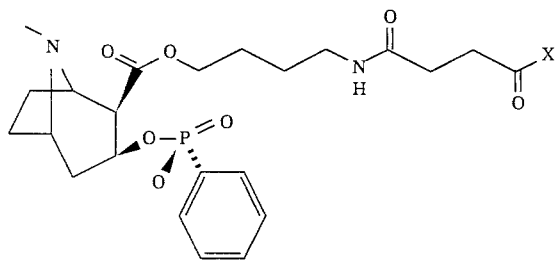

wherein X is a primary amine of a carrier protein.

7. A compound having the structure:

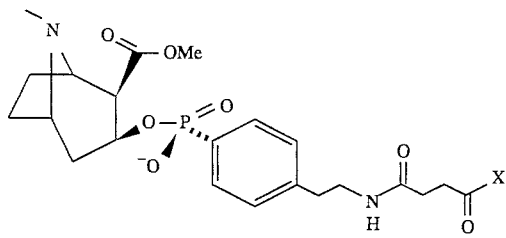

wherein X is a primary amine of a carrier protein.

8. A compound having the structure:

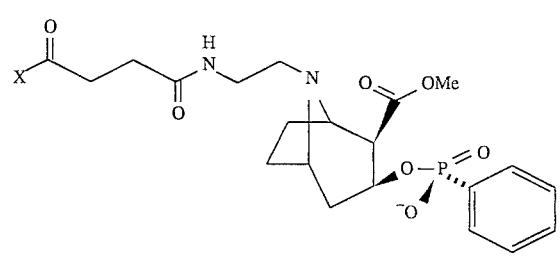

wherein X is a primary amine of a carrier protein.

9. The compound of any of claims 5, 6, 7, or 8 wherein the carrier protein is bovine serum albumin, bovine serum ovalbumin, keyhole limpet hemocyanin or thyroglobulin.

10. A method of synthesizing the compound of claim 6 comprising selectively alkylating:

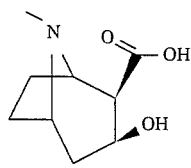

with 4-iodo-n-butyl azide, in the presence of tetraethyl ammonium hydroxide, to yield:

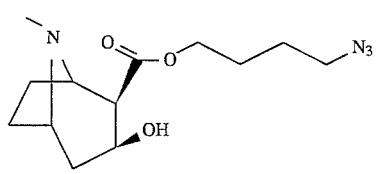

to which was added sequentially an equivalent of phenylphosphonic dichloride and methanol, in the presence of 1H-tetrazole, to obtain:

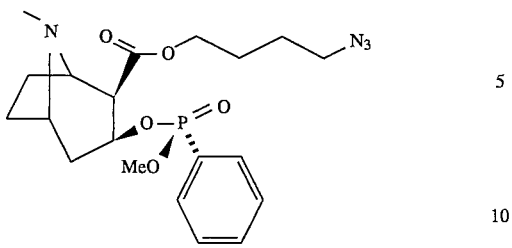
which was subsequently reduced with trimethyl phosphine in benzene to obtain:
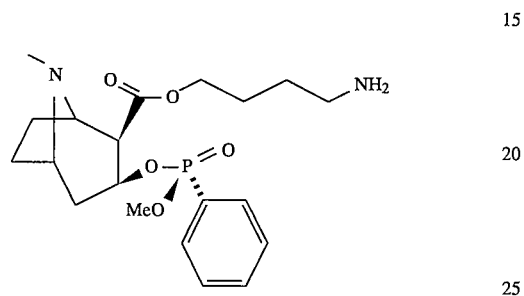
which was acylated with succinic anhydride to obtain:
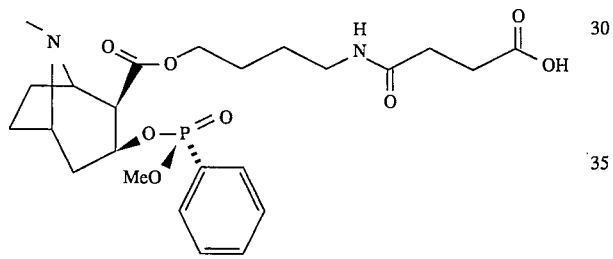
which was converted by acylation with N-hydrophthalimide in combination with dicyclohexylcarbodiimide to:
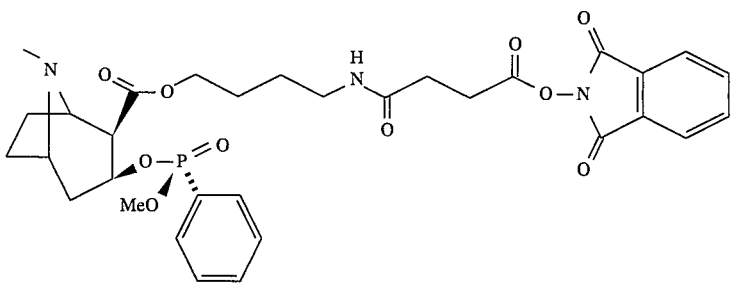
which was selectively dealkylated to:

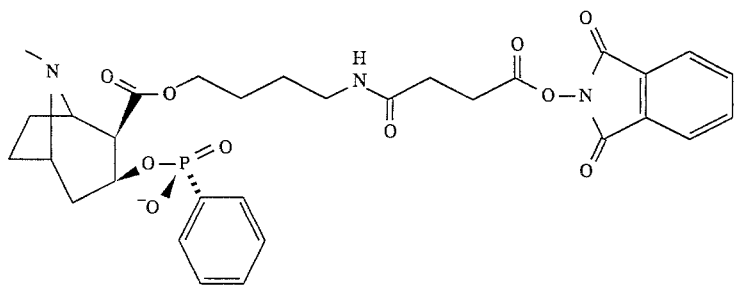

which was coupled to the primary amine of a carrier protein.

11. A method of synthesizing the compound of claim 7 comprising starting with the structure:

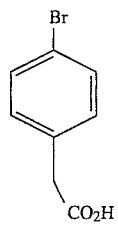

(a) esterifying with this acid with acidic methanol; (b) reducing the esterified acid with Dibal(Diisobutylaluminum hydride) to the corresponding alcohol; (c) protecting the alcohol with t-butyldimethylsilyl chloride under imidazole catalysis to yield A:

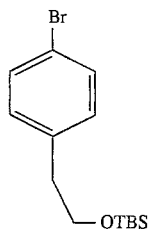

from the starting alcohol; (d) transmetalating A with n-butyl lithium to the following lithium B:

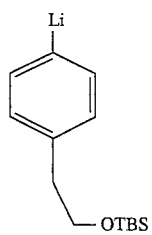

; (e) phosphorylating B with diethylchlorophosphate to yield C:

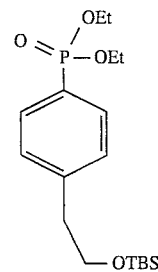

(f) removing the silyl group of (C) with tetra-n-butylammonium fluoride to yield the corresponding alcohol from (B); (g) transforming this alcohol to the bromide via tosylate; (h) converting the phosphonate ester from ethyl to methyl via bromotrimethylsilane followed by methanol; (i) displacing the bromide by azide; (j) transforming the phosphonate ester to the phosphorylchloride with the following structure D:

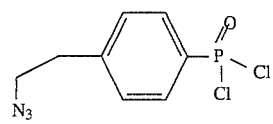

; (k) coupling D by the tetrazole catalysis method with methyl ecgonine:

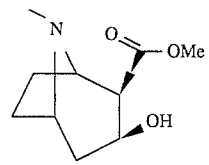

; (l) treating the coupled D with methanol to yield the mixed diester E in 30% yield after column chromatography, having the following structure:

E

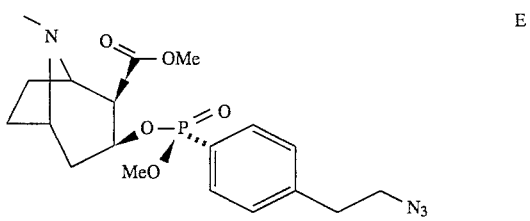

; (m) reducing the azide of E to the corresponding amine with triphenylphosphine; (n) coupling the amine to $^{14}C$ labeled succinic anhydride; (o) converting the resulting acid to its benzyl ester to facilitate column chromatography from E; and (p) removing the benzyl ester by catalytic hydrogenation.

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao It is certified that error appears in the above-indentified patent and that said Letters Patent is hereby corrected as shown below:

ON THE TITLE PAGE:
Item [56] Other Publications; immediately following
"E.J. Ziegler, et al. "Treatment of gram-negative bacteremia and septic shock with HA-1A human monoclonal antibody against",
"endotoxic" should read --endotoxin--.

Column 5, lines 6-19, the structure should read:

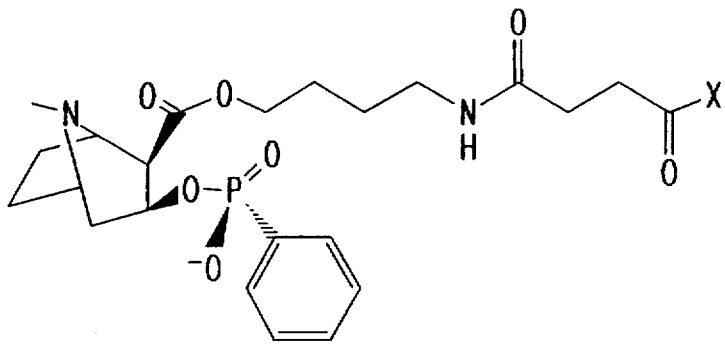

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao It is certified that error appears in the above-indentified patent and that said Letters Patent is hereby corrected as shown below:

Column 5, lines 21-33, the structure should read:

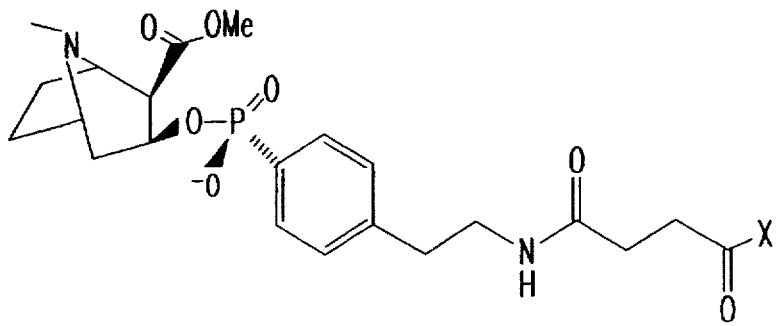

UNITED STATES PATENT AND TRADEMARK OFFICE
CERTIFICATE OF CORRECTION

PATENT NO. : 5,463,028

DATED : October 31, 1995

INVENTOR(S) : Donald W. Landry and Kang Zhao

It is certified that error appears in the above-indentified patent and that said Letters Patent is hereby corrected as shown below:

Column 5, lines 47-47, the structure should read:

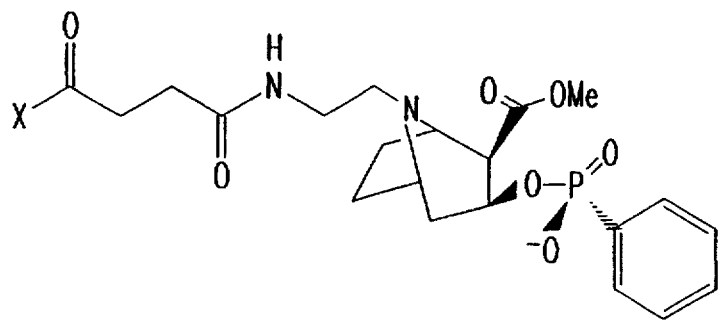

UNITED STATES PATENT AND TRADEMARK OFFICE
CERTIFICATE OF CORRECTION

PATENT NO. : 5,463,028

DATED : October 31, 1997

INVENTOR(S) : Donald W. Landry and Kang Zhao

It is certified that error appears in the above-indentified patent and that said Letters Patent is hereby corrected as shown below:

Column 5, immediately following "wherein X is a primary amine of a carrier protein.", the structure should read:

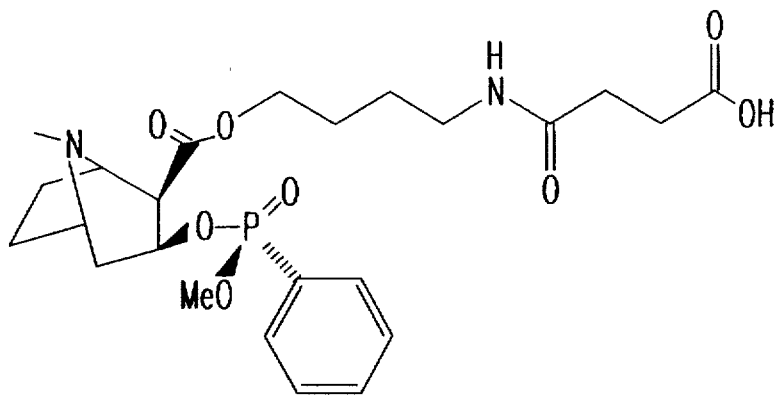

Column 6, line 38, "or $R_3$ is a trinitro lower alkyl azide group, a lower alkyl" should read --or $R_3$ is a lower alkyl azide group, a lower alkyl--.

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao It is certified that error appears in the above-indentified patent and that said Letters Patent is hereby corrected as shown below:

Column 7, lines 1-24, the structure should read:

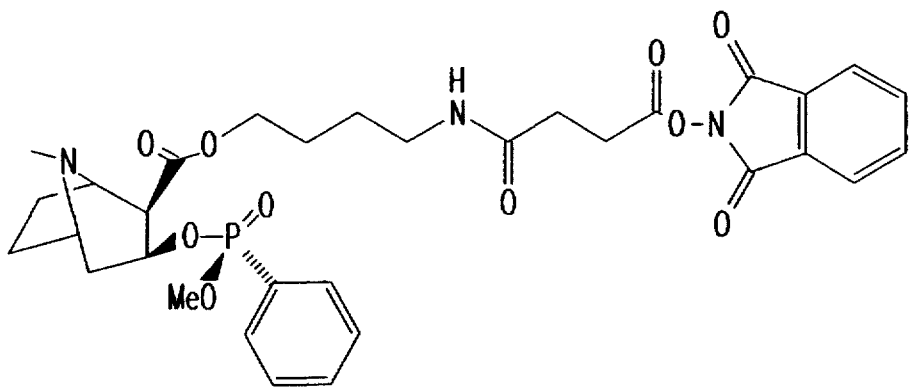

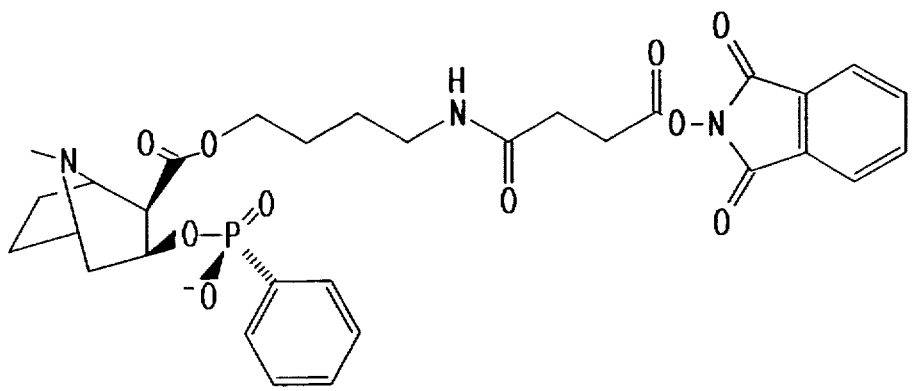

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao It is certified that error appears in the above-indentified patent and that said Letters Patent is hereby corrected as shown below:

Column 7, lines 41-53, the structure should read:

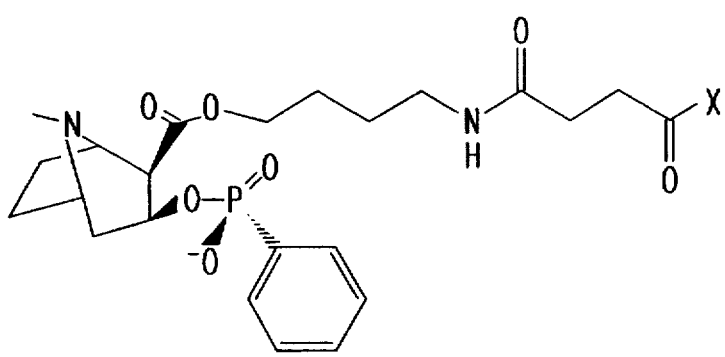

Column 11, lines 1-9, the structure should read:

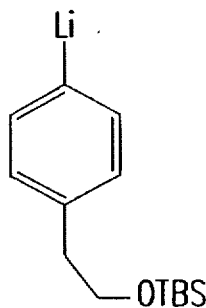

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao It is certified that error appears in the above-indentified patent and that said Letters Patent is hereby corrected as shown below:

Column 22, line 18, "10⁴" should read --$10^4$--.
Column 25, line 22, "convertion" should read --conversion--.
Column 34, line 29, "9 241-245" should read --9:241-245--.
Column 34, line 35, "40:426-433" should read --240:426-433--.
Column 34, line 36 "Immunosuppress ion" should read --Immunosuppression--.
Column 42, lines 46-54, in claim 11 (k), the structure should read:

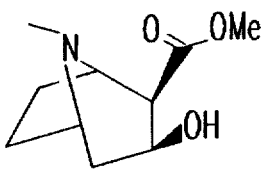

Column 42, lines 58-65, in claim 11 (l), the structure should read:

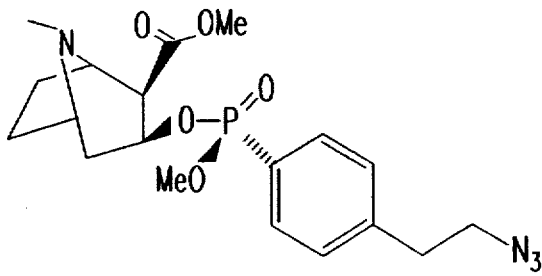

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao It is certified that error appears in the above-indentified patent and that said Letters Patent is hereby corrected as shown below:

Column 3, lines 30-40, the structure shown should be changed to:

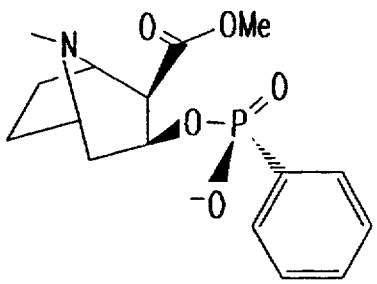

Column 7, lines 28-35, the structure shown should read:

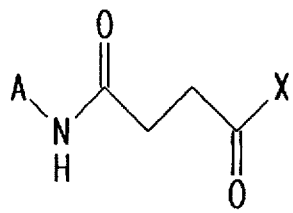

UNITED STATES PATENT AND TRADEMARK OFFICE
CERTIFICATE OF CORRECTION

PATENT NO.   : 5,463,028
DATED        : October 31, 1995
INVENTOR(S)  : Donald W. Landry and Kang Zhao It is certified that error appears in the above-indentified patent and that said Letters Patent is hereby corrected as shown below:

Column 8, lines 41-53, the structure should read:

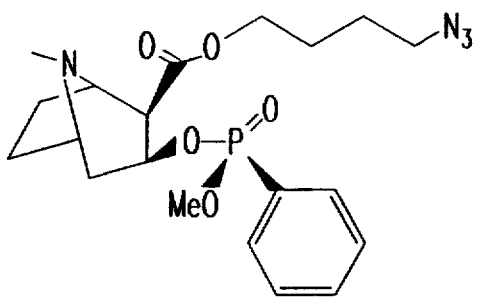

Column 8, lines 55-65, the structure should read:

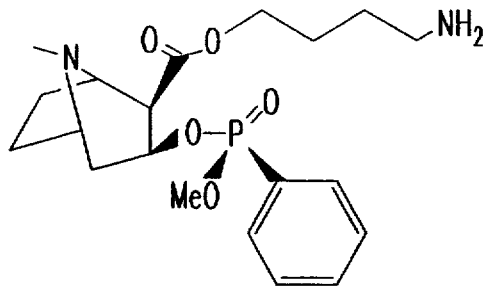

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao It is certified that error appears in the above-indentified patent and that said Letters Patent is hereby corrected as shown below:

Column 9, lines 1-10, the structure should read:

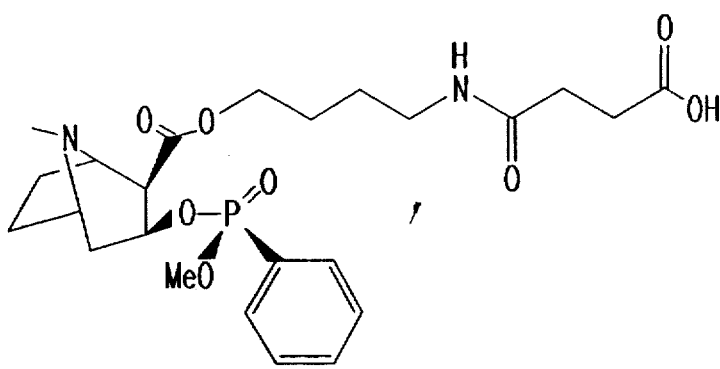

Column 9, immediately following "in combination with dicyclohexylcarbodiimide to:", the structure should read:

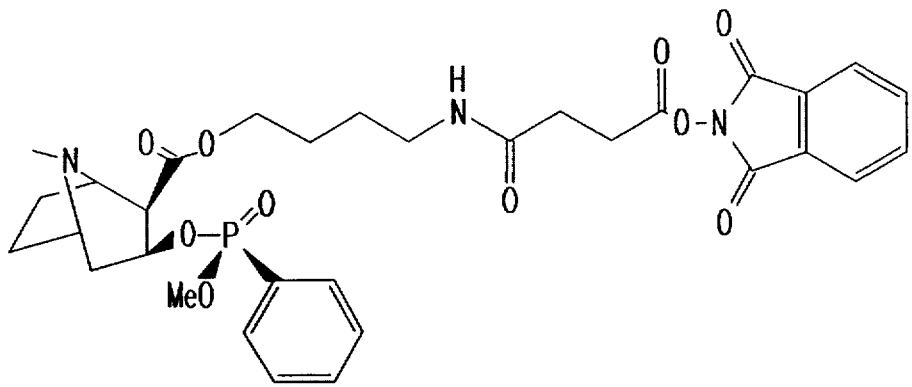

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao It is certified that error appears in the above-indentified patent and that said Letters Patent is hereby corrected as shown below:

Column 9, immediately following "which was selectively dealkylated to:", the structure should read:

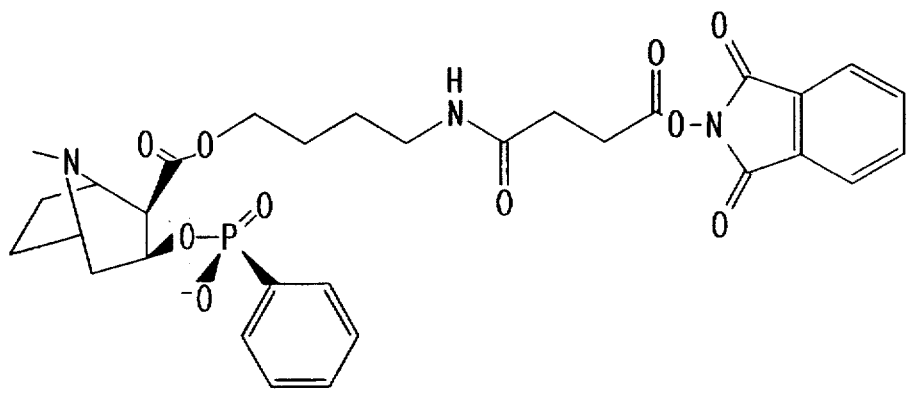

UNITED STATES PATENT AND TRADEMARK OFFICE
CERTIFICATE OF CORRECTION

PATENT NO. : 5,463,028

DATED : October 31, 1995

INVENTOR(S) : Donald W. Landry and Kang Zhao

It is certified that error appears in the above-indentified patent and that said Letters Patent is hereby corrected as shown below:

Column 15-16, in Scheme V, the molecules labeled 5, 6, and 7 should be changed to:

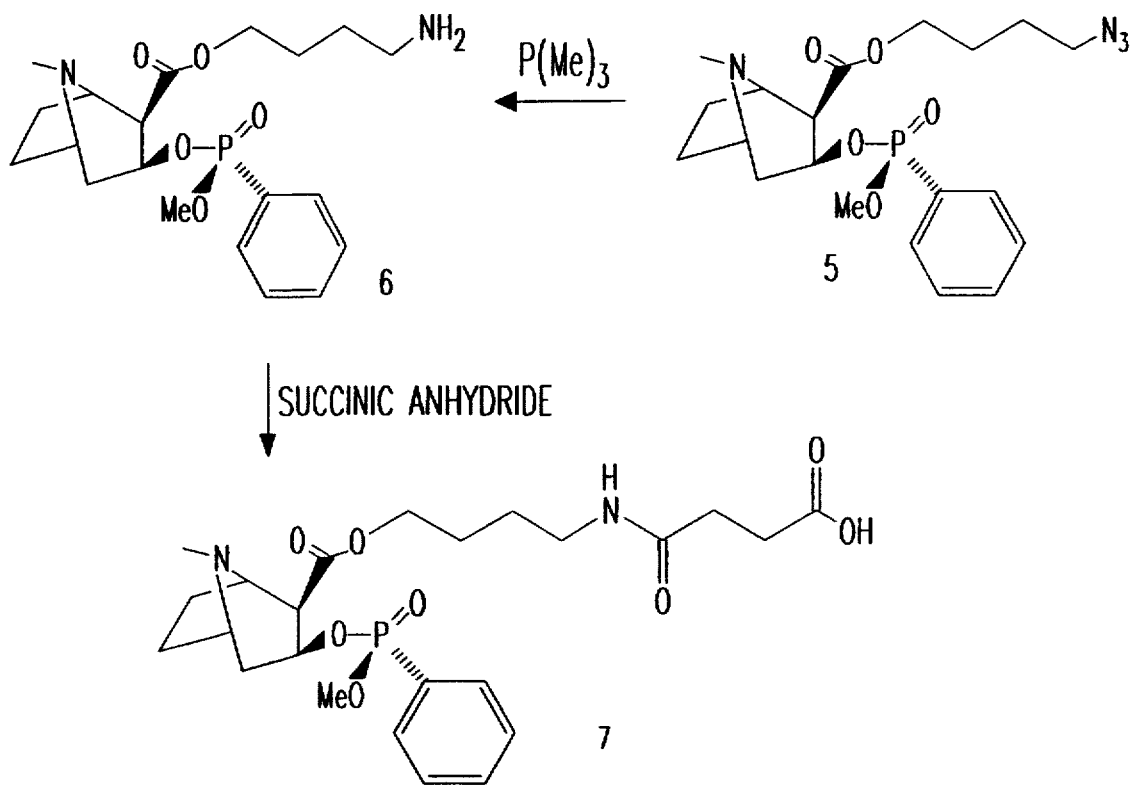

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao It is certified that error appears in the above-indentified patent and that said Letters Patent is hereby corrected as shown below:

Column 17 and 18, in the continuation of Scheme V, the molecule labeled 8 should be changed to:

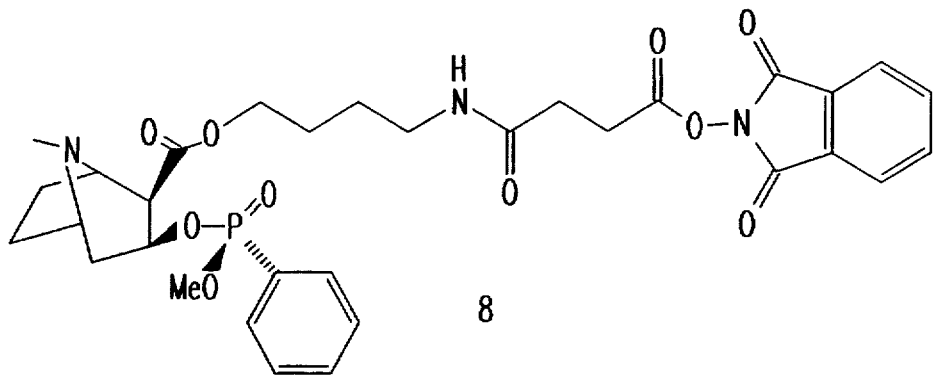

Column 20, line 17, "CH$^2$Cl$^2$" should read --CH$_2$Cl$_2$--.
Column 21, line 18, "synthesize" should read --synthesis--.
Column 28, line 49, "on" should read --one--.
Column 30, line 12, "pH2" should read --pH 2--.
Column 30, line 17-18, "non linear" should read --non-linear--.
Column 33, line 2, "315:1438-1443." should read 315:1438-1443 (1986)--.
Column 33, line 4, "307:1153, (1982)" should read --307:1153 (1982)--.
Column 33, line 5, "Pharmacology" should read --pharmacology--.
Column 33, line 14, "M.D. Wilson" should read --M.C. Wilson--.
Column 33, line 36, "252:708-(1974)" should read --252:708-710 (1974)--.

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao It is certified that error appears in the above-indentified patent and that said Letters Patent is hereby corrected as shown below:

```
Column 33, line 49, "250:1135 (1990)" should read --
250:1135-1139 (1990)--.
Column 33, line 50, "K.d. Janda et al." should read --
K.D. Janda et al.--.
Column 33, line 61, "Antibody-Catalyzed" should read -
-Antibody-catalyzed--.
Column 33, line 64, "acyltransfor" should read --
acyltransfer--.
Column 34, line 9, "anigens" should read --antigens--.
Column 34, line 18, "R.A. Fujii, et al" should read --
I. Fujii, et al.--.
Column 34, line 19, "113:8538-8529" should read
113:8528-8529--.
Column 34, line 39 "HalA" should read --Ha-1A--.
Column 34, line 42, "Wuitans" should read --Quintans--
.
Column 34, line 57, "maed" should read --mixed--.
Column 34, line 57, "phenly phosphonic" should read --
phenylphosphonic--.
Column 34, line 62, "36:1617 (198)" should read --
36:1617-1626 (1980)--.
Column 34, line 65, "29:169 (1987)" should read --
29:169-178 (1987)--.
Column 34, line 66, "S. Keda" should read --S. Ikeda--
.
Column 34, line 66, "A symmetric" should read --
Asymmetric--.
Column 35, line 6, "Total synthesis of 8S" should read
--Total synthesis of (±)-8S--.
Column 35, line 8, "Development" should read --
development--.
Column 35, line 17, "PharaKinetics" should read --
Pharmacokinetics--.
```

UNITED STATES PATENT AND TRADEMARK OFFICE
CERTIFICATE OF CORRECTION

PATENT NO. : 5,463,028
DATED : October 31, 1995
INVENTOR(S) : Donald W. Landry and Kang Zhao

It is certified that error appears in the above-indentified patent and that said Letters Patent is hereby corrected as shown below:

Column 37, lines 37-50, the structure should read:

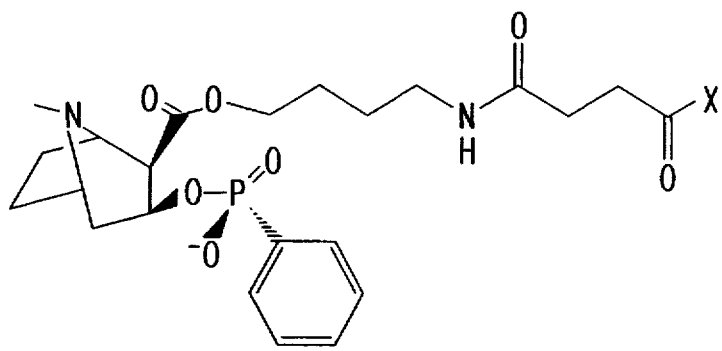

Signed and Sealed this

Twenty-fourth Day of November, 1998

Attest:

BRUCE LEHMAN

Attesting Officer

Commissioner of Patents and Trademarks